United States Patent
Leysieffer et al.

(10) Patent No.: US 6,575,894 B2
(45) Date of Patent: Jun. 10, 2003

(54) AT LEAST PARTIALLY IMPLANTABLE SYSTEM FOR REHABILITATION OF A HEARING DISORDER

(75) Inventors: Hans Leysieffer, Taufkirchen (DE); Bernd Waldmann, München (DE)

(73) Assignee: Cochlear Limited, Lanecove (AU)

( * ) Notice: Subject to any disclaimer, the term of this patent is extended or adjusted under 35 U.S.C. 154(b) by 190 days.

(21) Appl. No.: 09/833,704

(22) Filed: Apr. 13, 2001

(65) Prior Publication Data

US 2002/0029070 A1 Mar. 7, 2002

(30) Foreign Application Priority Data

Apr. 13, 2000 (DE) .......................................... 100 18 361

(51) Int. Cl.⁷ .............................................. H04R 25/00
(52) U.S. Cl. ....................................................... 600/25
(58) Field of Search .............................. 607/55–57, 137; 600/25

(56) References Cited

U.S. PATENT DOCUMENTS

| | | |
|---|---|---|
| 3,557,775 A | 1/1971 | Mahoney |
| 3,712,962 A | 1/1973 | Epley |
| 3,764,748 A | 10/1973 | Branch et al. |
| 4,352,960 A | 10/1982 | Dormer et al. |
| 4,441,210 A | 4/1984 | Hochmair et al. |
| 4,988,333 A | 1/1991 | Engebretson et al. |
| 5,015,224 A | 5/1991 | Maniglia |
| 5,015,225 A | 5/1991 | Hough et al. |
| 5,061,282 A | 10/1991 | Jacobs |
| 5,070,535 A | 12/1991 | Hochmair et al. |
| 5,095,904 A | 3/1992 | Seligman et al. |
| 5,113,859 A | 5/1992 | Funke |

(List continued on next page.)

FOREIGN PATENT DOCUMENTS

| | | |
|---|---|---|
| DE | 296 16 956 | 2/1997 |
| EP | 0 190 836 | 8/1986 |
| EP | 0 200 321 | 11/1986 |
| EP | 0 263 254 | 4/1988 |
| EP | 0 537 385 | 4/1993 |
| EP | 0 823 188 | 2/1997 |
| WO | 90/07251 | 6/1990 |

OTHER PUBLICATIONS

M. Fink, "Time–Reversed Acoustics", pp. 67–73, 1999, Scientific American.

H. Knoer, "Tinnitus Retraining Therapy and Hearing Acoustics", pp. 26–27, Feb. 1997, Journal Hörakustik.

(List continued on next page.)

Primary Examiner—Mark Bockelman
(74) Attorney, Agent, or Firm—Nixon Peabody LLP; David S. Safran

(57) ABSTRACT

An at least partially implantable system for rehabilitation of a hearing disorder with at least one sensor for picking up an acoustic signal and converting the acoustic signal into corresponding electrical signals, an electronic signal processing unit for audio signal processing and amplification, an electrical power supply unit which supplies energy to individual components of the system, and an output-side electromechanical transducer arrangement which consists of at least two independent and spatially separate transducers for stimulation of the inner ear. In conformity with the invention, the output-side electromechanical transducers are designed for stimulation of the fluid-filled inner ear spaces of the damaged inner ear and the signal processing unit comprises driving signal processing electronics which electrically controls each of the transducers such that a traveling wave configuration is formed on the basilar membrane of the damaged inner ear. The traveling wave configuration approximates the formation of a traveling wave of a healthy, undamaged inner ear.

66 Claims, 11 Drawing Sheets

U.S. PATENT DOCUMENTS

| | | | |
|---|---|---|---|
| 5,271,397 A | | 12/1993 | Seligman et al. |
| 5,277,694 A | | 1/1994 | Leysieffer et al. |
| 5,279,292 A | | 1/1994 | Baumann et al. |
| 5,360,388 A | | 11/1994 | Spindel et al. |
| 5,411,467 A | | 5/1995 | Hortmann et al. |
| 5,597,380 A | | 1/1997 | McDermott et al. |
| 5,601,617 A | | 2/1997 | Loeb et al. |
| 5,603,726 A | | 2/1997 | Schulman et al. |
| 5,624,376 A | | 4/1997 | Ball et al. |
| 5,626,629 A | | 5/1997 | Faltys et al. |
| 5,772,575 A | | 6/1998 | Lesinski et al. |
| 5,795,287 A | | 8/1998 | Ball et al. |
| 5,814,095 A | | 9/1998 | Müller et al. |
| 5,881,158 A | * | 3/1999 | Lesinski et al. ............ 381/174 |
| 5,951,601 A | | 9/1999 | Lesinski et al. |
| 5,977,689 A | | 11/1999 | Neukermans |
| 5,984,859 A | | 11/1999 | Lesinski |
| 5,997,466 A | | 12/1999 | Adams et al. |
| 5,999,632 A | | 12/1999 | Leysieffer et al. |
| 6,005,955 A | | 12/1999 | Kroll et al. |
| 6,068,589 A | * | 5/2000 | Neukermans ................ 600/25 |
| 6,123,660 A | | 9/2000 | Leysieffer |
| 6,131,581 A | | 10/2000 | Leysieffer et al. |
| 6,198,971 B1 | | 3/2001 | Leysieffer |
| 6,227,204 B1 | | 5/2001 | Baumann et al. |
| 6,251,062 B1 | | 6/2001 | Leysieffer |

OTHER PUBLICATIONS

E. Lehnhardt, "Intracochlear Placement of Cochlear Implant Electrodes in Soft Surgery Technique", pp. 356–359, 1993, HNO vol. 41.

H. Leysieffer et al., "A Totally Implantable Hearing Device for the Treatment of Sensorineural Hearing Loss", pp. 853–863, 1998, TICA LZ 3001, in vol. 46.

J. Müller–Deile et al., "Cochlear Implant Supply for Non–Deaf Patients?", pp. 136–146, 1998, Laryngo–Rhino–Otol., vol. 77.

E. Le Page et al., "Non–Linear Mechanical Behavior of the Basilar Membrane in the Basal Turn of the Guinea Pig Cochlea", pp. 183–189, 1980, Hearing Research 2.

S. Ruh et al., "Cochlear Implant for Patients with Residual Hearing", pp. 347–350, 1997, Laryngo–Rhino–Otol., vol. 76.

N. Yanagihara et al., "Implantable Hearing Aid", pp. 869–872, Aug. 1987, Arch Otolaryngol Head Neck Surg–vol. 113.

H.P. Zenner et al., "First Implantations of a Totally Implantable Electronic Hearing System for Sensorineural Hearing Loss", pp. 844–852, 1998, HNO vol. 46.

H.P. Zenner, "Physiology, Biochemistry, Cell and Neurobiology", pp. 107–108, 1994, Hören, Georg Thieme Verlga Stuttgart–New York.

H.P. Zenner et al., "Active Electronic Hearing Implants for Patients with Conductive and Sensorineural Hearing Loss–a New Era of Ear Surgery", pp. 749–757, 1997, HNO vol. 45.

H.P. Zenner et al., "Totally Implantable Hearing Device for Sensorineural Hearing Loss", p. 1751, Nov. 28, 1998, The Lancet vol. 352, No. 9142.

* cited by examiner

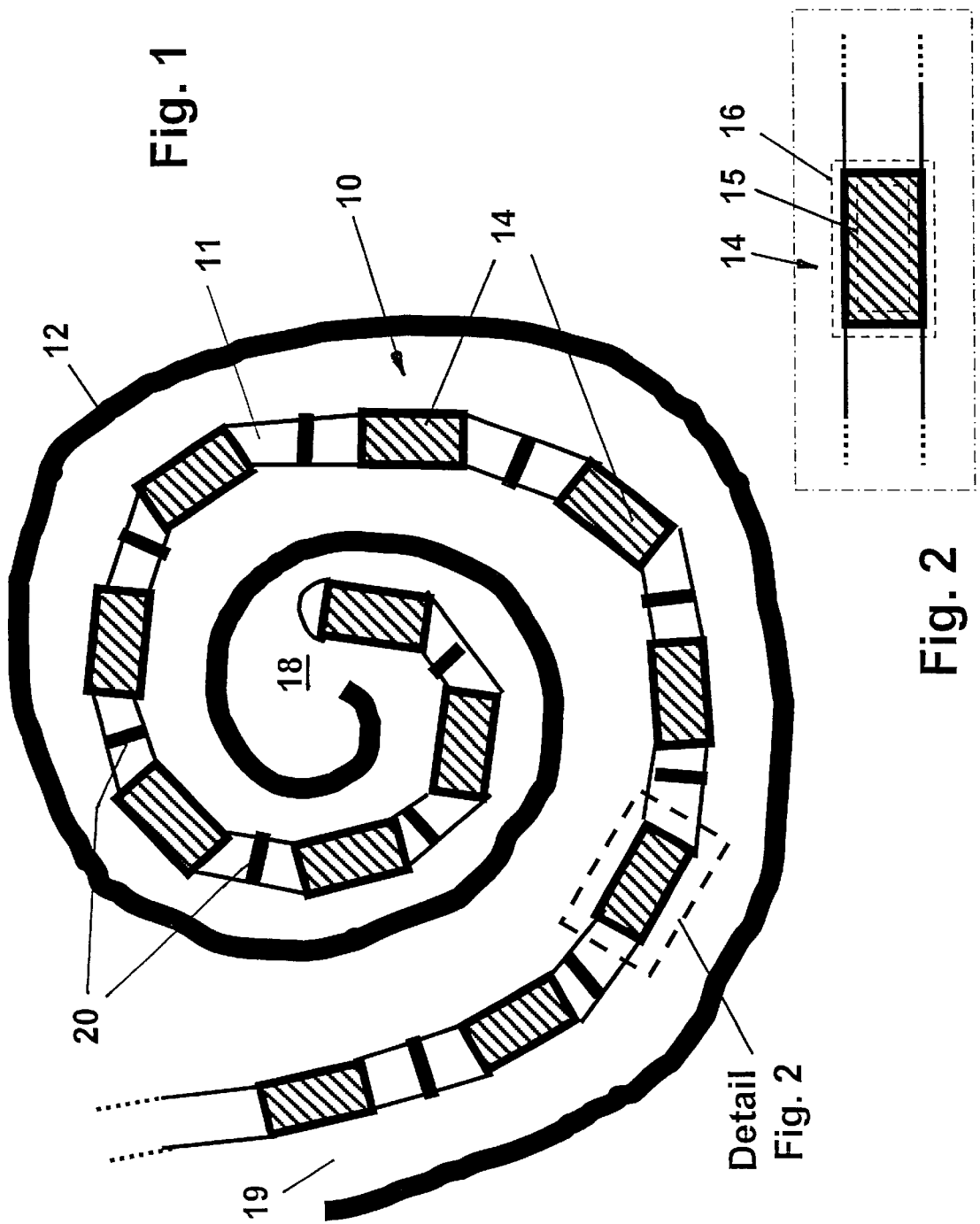

AT LEAST PARTIALLY IMPLANTABLE SYSTEM FOR REHABILITATION OF A HEARING DISORDER

BACKGROUND OF THE INVENTION

1. Field of the Invention

This invention relates to an at least partially implantable system for rehabilitation of a hearing disorder comprising at least one sensor (microphone) for picking up an acoustic signal and converting the acoustic signal into corresponding electrical signals, an electronic arrangement for audio signal processing and amplification, an electrical power supply unit which supplies individual components of the system with current, and an output-side electromechanical transducer arrangement which consists of at least two independent and spatially separate transducers for stimulation of the inner ear.

2. Description of Related Art

The expression "hearing disorder" is defined here as inner ear damage, combined inner ear and middle ear damage, and a temporary or permanent noise impression (tinnitus).

In recent years, rehabilitation of sensorineural hearing disorders with partially implantable electronic systems has acquired major importance. In particular, this applies to the group of patients in which hearing has completely failed due to accident, illness or other effects or in which hearing is congenitally non-functional. If, in these cases, only the inner ear (cochlea), and not the neural auditory path which leads to the brain, is affected, the remaining auditory nerve can be stimulated with electrical stimulation signals. Thus, a hearing impression can be produced which can lead to speech comprehension. In these so-called cochlear implants (CI), an array of stimulation electrodes, which is controlled by an electronic system (electronic module), is inserted into the cochlea. This electronic module is encapsulated with a hermetic, biocompatible seal and is surgically embedded in the bony area behind the ear (mastoid). The electronic system contains essentially only decoder and driver circuits for the stimulation electrodes. Acoustic sound reception, conversion of this acoustic signal into electrical signals and their further processing, always takes place externally in a so-called speech processor which is worn outside on the body. The speech processor converts the preprocessed signals into a high frequency carrier signal which, via inductive coupling, is transmitted through the closed skin (transcutaneously) to the implant. The sound-receiving microphone is always located outside of the body and, in most applications, in a housing of a behind-the-ear hearing aid worn on the external ear. The microphone is connected to the speech processor by a cable. Such cochlear implant systems, their components, and the principles of transcutaneous signal transmission are described, by way of example, in Published European Patent Application EP 0 200 321 A2 and in U.S. Pat. Nos. 5,070,535, 4,441,210 and 5,626,629. Processes of speech processing and coding in cochlear implants are described, for example, in Published European Patent Application EP 0 823 188 A1, in European Patent EP 0 190 836 A1 and in U.S. Pat. Nos. 5,597,380, 5,271,397, 5,095,904, 5,601,617 and 5,603,726.

In addition to rehabilitation of congenitally deaf persons and those who have lost their hearing using cochlear implants, for some time there have been approaches to offer better rehabilitation than with conventional hearing aids to patients with a sensorineural hearing disorder which cannot be surgically corrected by using partially or totally implantable hearing aids. The principle consists, in most embodiments, in stimulating an ossicle of the middle ear or, directly, the inner ear via mechanical or hydromechanical stimulation and not via the amplified acoustic signal of a conventional hearing aid in which the amplified acoustic signal is supplied to the external auditory canal. The actuator stimulus of these electromechanical systems is accomplished with different physical transducer principles such as, for example, by electromagnetic and piezoelectric systems. The advantage of these devices is seen mainly in the sound quality which is improved compared to conventional hearing aids, and, for totally implanted systems, in the fact that the hearing prosthesis is not visible.

Such partially and totally implantable electromechanical hearing aids are described, for example, by Yanigahara and Suzuki et al. (Arch Otolaryngol Head Neck, Surg—Vol 113, August 1987, pp. 869–872; Hoke M. (ed.), Advances in Audiology, Vol. 4, Karger Basel, 1988), H. P. Zenner et al. "First implantations of a totally implantable electronic hearing system for sensorineural hearing loss", in HNO Vol. 46, 1998, pp. 844–852; H. Leysieffer et al. "A totally implantable hearing device for the treatment of sensorineural hearing loss: TICA LZ 3001", in HNO Vol. 46, 1998, pp. 853–863; H. P. Zenner et al. "Active electronic hearing implants for patients with conductive and sensorineural hearing loss—a new era of ear surgery" HNO 45, 1997, pp. 749–774; H. P. Zenner et al. "Totally implantable hearing device for sensorineural hearing loss", The Lancet Vol. 352, No. 9142, page 1751; and described in numerous patent documents among others in Published European Patent Applications EP 0 263 254 A1, EP 0 400 630 A1, and EP 0 499 940 A1, and in U.S. Pat. Nos. 3,557,775, 3,712,962, 3,764,748, 5,411,467, 4,352,960, 4,988,333, 5,015,224, 5,015,225, 5,360,388, 5,772,575, 5,814,095, 5,951,601, 5,977,689 and 5,984,859. Here, the insertion of an electromechanical transducer through an opening in the promontory for direct fluid stimulation in the inner ear is described in U.S. Pat. Nos. 5,772,575, 5,951,601, 5,977,689 and 5,984,859.

Many patients with inner ear damage also suffer from temporary or permanent noise impressions (tinnitus) which cannot be surgically corrected and for which, to date, there are no approved drug treatments. Therefore, so-called tinnitus maskers (WO-A 90/07251, Published European Patent Application EP 0 537 385 A1, German Utility Model No. 296 16 956) are known. These devices are small, battery-driven devices which are worn like a hearing aid behind or in the ear and which, by means of artificial sounds which are emitted, for example, via a hearing aid speaker into the auditory canal, psychoacoustically mask the tinnitus and thus reduce the disturbing noise impression, if possible, to below the threshold of perception. The artificial sounds are often narrowband noise (for example, third-band noise) The spectral position and the loudness level of the noise can be adjusted via a programming device to enable adaptation to the individual tinnitus situation as optimally as possible. In addition, the so-called retraining method has been developed recently in which, by combination of a mental training program and presentation of broadband sound (noise) near the auditory threshold, the perceptibility of the tinnitus in quiet conditions is likewise supposed to be largely suppressed (H. Knoer "Tinnitus retraining therapy and hearing acoustics" journal "Hoerakustik" February 1997, pages 26 and 27). These devices are also called "noisers".

In the two aforementioned methods for hardware treatment of tinnitus, hearing aid-like, technical devices must be carried visibly outside on the body in the area of the ear; they stigmatize the wearer and, therefore, are not willingly worn.

U.S. Pat. No. 5,795,287 describes an implantable tinnitus masker with direct drive of the middle ear, for example, via an electromechanical transducer coupled to the ossicular chain. This directly coupled transducer can preferably be a so-called "Floating Mass Transducer" (FMT). This FMT corresponds to the transducer for implantable hearing aids which is described in U.S. Pat. No. 5,624,376.

In commonly owned co-pending U.S. patent application Ser. Nos. 09/372,172 and 09/468,860, which are hereby incorporated by reference, implantable systems for treatment of tinnitus by masking and/or noiser functions are described, in which the signal-processing electronic path of a partially or totally implantable hearing system is supplemented by corresponding electronic modules such that the signals necessary for tinnitus masking or noiser functions can be fed into the signal processing path of the hearing aid function and the pertinent signal parameters can be individually adapted by further electronic measures to the pathological requirements. This adaptability can be accomplished by storing or programming the necessary setting data of the signal generation and feed electronics by using hardware and software in the same physical and logic data storage area of the implant system, and by controlling the feed of the masker or noiser signal into the audio path of the hearing implant via the corresponding electronic actuators.

Depending on the desired function, implantable rehabilitation devices of the aforementioned type consist of several functional units, especially: (1) a sensor (microphone) which converts the incident airborne sound into an electrical signal; (2) an electronic signal processing, amplification and implant control unit; (3) an implantable electromechanical or electroacoustic transducer which converts the amplified and preprocessed sensor signals into mechanical or acoustic vibrations and sends them via suitable coupling mechanisms to the damaged middle and/or inner ear, or, in the case of cochlear implants, a cochlear stimulation electrode; and (4) an electric power supply system which supplies the aforementioned modules. Furthermore, there can be an external unit which makes available electrical recharging energy to the implant when the implant-side power supply unit contains a rechargeable (secondary) battery. Especially advantageous devices and processes for charging rechargeable implant batteries are described in commonly owned co-pending U.S. patent application Ser. No. 09/311,566 and in commonly owned U.S. Pat. No. 5,279,292, which are hereby incorporated by reference. Preferably, there can also be a telemetry unit with which patient-specific, audiological data can be wirelessly transmitted bi-directionally or programmed in the implant and thus permanently stored, as was described by Leysieffer et al. in HNO Vol. 46, 1998, pp. 853–863.

Basically, in all these at least partially implantable systems, the (audio) signal processing or signal generation and the implant control modules, such as, for example, a controlled battery recharging system or a telemetry system for bidirectional transmission of, for example, variable, patient-specific parameters, are accomplished on the implant-side by permanently fixed hardware units. This also applies when digital signal processors, microcontrollers or microprocessors are used for signal processing, signal generation or for implant management, regardless of whether they are built as so-called "hardwired logic", i.e. in "hardwired" logic architecture, or whether their operating programs are stored in the read-only memory areas (for example, ROM) of the corresponding processors. These programs, which are provided and are necessary for basic operation of the implant and for the intended functions, are hereinafter called the operating program or the operating software. In the known implant systems, this operating software is placed in the system during production, for example, by mask programming of processor storage areas and can no longer be changed after implantation.

In contrast thereto, patient-specific data such as, for example, audiological adaptation data or variable implant system parameters (for example, a variable in one of the aforementioned software programs for control of battery recharging) are herein called operating parameters. In known totally implantable implant systems after implantation, these operating parameters can be transmitted transcutaneously, i.e. wirelessly through the closed skin, to the implant and thus can be changed.

The above described at least partially implantable hearing systems for rehabilitation of inner ear damage, which are based on an output-side electromechanical transducer, differ from conventional hearing aids essentially only in that the output-side acoustic stimulus (i.e., an amplified acoustic signal in front of the eardrum) is replaced by an amplified mechanical stimulus of the middle ear or inner ear. The acoustic stimulus of a conventional hearing aid ultimately leads to vibratory, i.e., mechanical, stimulation of the inner ear, via mechanical stimulation of the eardrum and the subsequent middle ear. The requirements for effective audio signal preprocessing are fundamentally similar or the same. Furthermore, in both embodiments on the output side a localized vibratory stimulus is ultimately routed to the damaged inner ear (for example, an amplified mechanical vibration of the stapes in the oval window of the inner ear).

Basically, in this routinely used rehabilitation of inner ear damage by active hearing systems (regardless of whether the rehabilitation is by an external acoustic stimulus or by an implanted electromechanical stimulus), at present there is a major disadvantage which is described below in summary for understanding of this invention: most cases of sensorineural hearing loss are based on more or less pronounced damage of the outer hair cells in the inner ear. These outer hair cells, which in large number are located in the organ of Corti along the basilar membrane, form part of the so-called cochlear amplifier which, depending on local stimulation of the basilar membrane as a result of traveling wave formation, actively mechanically de-attenuates this local stimulation range at low levels and thus small traveling wave amplitudes, which leads to an increase in sensitivity. This active amplification is based on a very complex, efferently controlled process which is not detailed here. It is furthermore assumed that at very high levels of inner ear stimulation as a result of high loudness, this effect is reversed in its action and thus locally reduces and actively attenuates the traveling wave amplitude. These nonlinear characteristics of the cochlear amplifier, which is located along the organ of Corti in several hundred functional units with locally limited action, are of decisive importance for the function of the healthy inner ear. In partial or total failure of the outer hair cells, in addition to a loss of sensitivity which leads to a rise in the hearing threshold, other defects arise: the described active de-attenuation of the basilar membrane leads to high Q-factors of the envelopes of the traveling waves which are essentially responsible for the frequency discrimination capacity (tone pitch differences). If these so-called shape tuning curves are lacking due to failure or partial damage of the outer hair cells, the affected individual can perceive tone pitch differences much more poorly. The rise of the hearing threshold leads, moreover, to a reduction of the dynamic range since the upper sensory threshold (discomfort threshold) in sensorineural hearing loss does not rise at the same time. This reduction of dynamics results in an increased perception of loudness, which is called positive recruitment. The described effects, which are caused by damage or failure of the outer hair cells, lead, in the overall effect for the affected individual, to a reduction in speech comprehension, especially in a noisy environment (summary description by H. P. Zenner: Hoeren, Georg Thieme Verlag Stuttgart, New York, 1994, pages 20–23, 107 and 108, and E. W. LePage, M. B. Johnstone: "Non-linear mechanical behavior of the basilar membrane in the basal turn of the guinea pig cochlea." Hearing Research 2 (1980), 183–189).

An important consequence of this described mechanism is that, as indicated above, both in conventional acoustic hearing aids and also in partially or totally implantable hearing systems, the important functions of the damaged outer hair cells and thus of the cochlear amplifier cannot be replaced or at least partially restored. U.S. Pat. No. 6,123,660 discloses a transducer arrangement for partially or totally implantable hearing aids for direct mechanical stimulation of the middle ear or inner ear, which is provided with a piezoelectric transducer element and also with an electromagnetic transducer which are accommodated in a common housing and which can be coupled via the same coupling element to a middle ear ossicle or directly to the inner ear.

Furthermore, implantable hearing systems are known (U.S. Pat. Nos. 5,997,466 and 6,005,955) which are provided with two or more output-side electromechanical transducers in a single arrangement or locally separate arrangements. These embodiments are, however, uniquely described in that the system design with more than one transducer enables a linear superposition of the deflection frequency responses of the individual transducers which, as a result, allows an output-side stimulation form of the cochlea which is spectrally optimized as much as possible or which is adjustable or programmable depending specifically on frequency, and which thus shall lead to a spectrally balanced and sufficient loudness impression of the implant system. Rehabilitation of the cochlear amplifier with the aforementioned features is, however, not possible by these embodiments or described signal preprocessing methods.

SUMMARY OF THE INVENTION

A primary object of this invention is to devise an at least partially implantable system for rehabilitation of a hearing disorder which is able to at least partially replace or restore the function of the cochlear amplifier.

In accordance with the invention, this object is achieved in an at least partially implantable system for rehabilitation of a hearing disorder which comprises: at least one sensor (microphone) for picking up the acoustic signal and for conversion thereof into corresponding electrical signals; an electronic signal processing unit for audio signal processing and amplification; an electrical power supply unit which supplies energy to individual components of the system; and an output-side electromechanical transducer arrangement which consists of at least two independent and spatially separate transducers for stimulation of the inner ear. By the output-side electromechanical transducers being designed for stimulation of the fluid-filled inner ear spaces of the damaged inner ear, and by the signal processing unit having driving signal processing electronics which electrically controls each of the transducers, such that on the basilar membrane of the damaged inner ear, a traveling wave configuration is formed which approximates the manner of the traveling wave formation of a healthy, undamaged inner ear.

Recently, it has become scientifically known from CI implantations that, even for incomplete deafness, cochlear implants (CIs) can be successfully used when sufficient speech discrimination can no longer be achieved with a conventional hearing aid. Interestingly, it was demonstrated that the important inner ear structures, which enable residual acoustic hearing capacity, can be maintained in part or in a largely stable condition over time when a CI electrode is inserted into the cochlea (S. Ruh et al.: "Cochlear implant for patients with residual hearing", Laryngo-Rhino-Otol. 76 (1997) 347–350; J. Mueller-Deile et al.: "Cochlear implant supply for non-deaf patients?" Laryngo-Rhino-Otol. 77 (1998) 136–143; E. Lehnhardt: "Intracochlear placement of cochlear implant electrodes in soft surgery technique", HNO 41 (1993), 356–359). This invention is based on these findings, to the extent that, in particular for sensorineural hearing loss which does not approach deafness, an electromechanical transducer array can be clinically and safely used in the cochlea (instead of an electrical stimulation electrode array) such that rehabilitation of inner ear damage by electronic simulation of the cochlear amplifier is possible with better results than in conventional acoustic hearing aids or implantable hearing systems according to the aforementioned prior art. Furthermore, with the presently disclosed multichannel hearing implant system, tinnitus, which can be at least peripherally localized, will also be more effectively masked than with known conventional tinnitus maskers.

Preferably, the output-side electromechanical transducers are designed for direct stimulation of the fluid-filled inner ear spaces of the damaged inner ear. This direct stimulation of the cochlea prevents or largely reduces the occurrence of feedback, i.e. coupling of the output signal into the sensor (microphone), because the ossicular chain, and thus the eardrum, are not excited by vibrations or at least are excited to a substantially reduced degree. This is especially advantageous when an acoustic sensor (microphone function) is applied in the immediate vicinity of the eardrum, as is known from U.S. Pat. Nos. 5,814,095 and 5,999,632.

Direct stimulation of the fluid-filled inner ear spaces of the damaged inner ear can be achieved especially by an intracochlear array of output-side electromechanical transducers. Such a transducer array is implanted directly into a fluid-filled space of the inner ear (scala tympani or scala vestibuli).

Preferably, the intracochlear transducer array has a total diameter in the range of 0.4 mm (apical area) to 2.0 mm (basal area) and a total length between 5 mm and 50 mm. Preferably, the intracochlear transducer array has a carrier of biocompatible material which is biostable in the inner ear, preferably a polymer, especially a silicone. The individual output-side electromechanical transducers can be embedded in the carrier for reasons of biocompatibility such that they are completely surrounded by a thin layer of the carrier material.

In order to minimize mechanical wave propagation from a transducer within the carrier to adjacent transducers, in a further development of the invention, mechanical attenuation elements are embedded in the carrier between the individual output-side electromechanical transducers. In the case of the attenuation elements having a cross sectional geometry similar to that of the carrier, the material of the attenuation elements preferably is chosen such that there is a high mechanical impedance difference relative to the carrier material in order to achieve high attenuation values.

The intracochlear transducer array or parts thereof (especially the transducers and/or the attenuation elements) can be produced using microsystems engineering.

According to a modified embodiment of the invention, there is an extracochlear multichannel array of output-side electromechanical transducers which is fixed on the cochlea from the outside thereof.

Such an extracochlear transducer array in its entirety can be developed and produced simply and with high precision in processes which are conventional in semiconductor manufacture art using microsystems engineering, for example, by photolithography. Such processes allow a high level of miniaturization and excellent reproducibility of the individual transducers on an array. The properties of production by Microsystems engineering are especially advantageous here, because in the intended function of the array, the phase synchronism of the individual transducers on the array is very important. Details of microsystems engineering processes are described, among others, in International Patent Application Publication WO-A-99/03146 and do not require further explanation here.

For the extracochlear transducer array, there can advantageously be provided a substrate which contains an electrical terminal panel which is produced at the same time using microsystems engineering and which is designed for connection of a multipole, biocompatible implant lead to a module which contains the driving signal processing electronics. The substrate of the extracochlear transducer array can furthermore be provided with an electronic module which was produced at the same time using Microsystems engineering and which can contain, especially driver stages for controlling the output-side electromechanical transducers and/or decoding logic and transducer modules for connection of a minimum pole implant lead. Thus, the array terminal can consist of only three lines, especially one ground line, one data line and one clock signal line. The supply of electrical operating energy can take place by phantom feed on the clock signal line or by rectifying the clock signal directly.

The electronic module can, furthermore, contain an interface module for digital data transmission via the implant lead, preferably by means of an optical fiber, and/or D/A converters and driver modules assigned to the transducers for serial data transmission on the implant feed lead.

Preferably, the extracochlear transducer array including the carrier structure (substrate) is equipped with biocompatible coating which preferably consists of polymers known from implant technology, especially polytetrafluoroethylene, polyurethane or silicones.

Direct stimulation of the fluid-filled inner ear spaces when using an extracochlear transducer array can be provided by the transducers each having an output-side coupling element which is made such that the coupling element projects through an artificial access to the inner ear (openings or holes in the bony outer wall of the cochlea, so-called "cochleostomia").

The output-side electromechanical transducers are preferably hermetically sealed and they basically can operate according to any known electromechanical transducer principle, and can be designed especially as electromagnetic, electrodynamic, piezoelectric, magnetostrictive or dielectric (capacitive) transducers. In particular for an extracochlear array embodiment, the piezoelectric principle and the dielectric or capacitive principle are especially preferred. When using the piezoelectric transducer principle, they are advantageously made using lead zirconate titanate ceramics or PVDF (polyvinylidene fluoride). In particular the output-side electromechanical transducers are preferably made using geometrical shape transformations, especially the bimorph principle, the unimorph principle or the heteromorph principle with passive material partners such that, at a given transducer voltage, they produce maximum deflection with minimum electric power consumption.

In another embodiment of the invention, the output-side electromechanical transducers in the pertinent transducer array are arranged distributed equidistantly or at logarithmic distances according to the tonotopic frequency-location assignment along the basilar membrane of the inner ear, and in the case of a tonotopic arrangement, a number of transducers from 20 to 24, according to psychoacoustic critical bands, can lead to especially favorable results.

The output-side electromechanical transducers preferably have a transmission range from about 100 Hz to about 10 kHz and they are preferably tuned high, i.e. their first mechanical resonant frequency is at the upper end of the desired transmission frequency range, especially at about 8 kHz to about 10 kHz. As a result, the deflection frequency response of the transducers in the transmission range is largely free of resonances and, in the case of voltage impression and use of piezoelectric transducers, is flat regardless of frequency. Thus, there is no ripple in the transmission range.

The signal processing unit preferably has a preprocessing arrangement for preamplification and/or filtering and for analog-digital (A/D) conversion of the acoustic sensor signals. The signal processing unit can in particular comprise anti-aliasing filters. If a plurality of acoustic sensors is used, preferably each of the acoustic sensors has an analog-digital converter connected to the output thereof In another embodiment of the invention, the signal processing unit can contain software modules which, parallel to a hearing aid operation, enable masking of tinnitus. With this multichannel hearing implant system, tinnitus, which can be at least peripherally localized, can be masked more effectively than with known conventional tinnitus maskers.

The signal processing unit advantageously has a digital signal processor for processing the A/D-converted acoustic sensor signals which have been optionally preprocessed by means of the preprocessing arrangement and/or for generation of digital signals for tinnitus masking, wherein at least one digital-analog-converter is associated to the output-side electromechanical transducer arrangement and wherein preferably each output-side electromechanical transducer has its own digital-analog converter connected to the output thereof.

In another embodiment of the invention, the signal processing electronics contain software modules which control the output-side electromechanical transducers such that the spectral, time, amplitude- and phase-referenced transducer signal properties are dimensioned such that a traveling wave is produced on the basilar membrane of the damaged inner ear and the traveling wave is as similar as possible to that of healthy hearing.

The software modules can be designed to be static such that, as a result of scientific findings, they are stored once in a program storage of the digital signal processor and remain unchanged. But if, for example, due to more recent scientific findings, improved algorithms for speech signal conditioning and processing are available and are desired to be used, the entire implant or implant module which contains the corresponding signal processing unit must be replaced by a new unit with the altered operating software by invasive surgery on the patient. This surgery entails renewed medical risks for the patient and is very costly.

This problem can be solved with another embodiment of the invention in that a wireless, preferably PC-based telemetry means is provided for transmission of data between the implanted part of the system and an external unit, especially an external programming system, wherein preferably a rewriteable implantable storage arrangement is assigned to the signal processor for accommodating and reproducing the operating program. Also, at least part of the operating program can be replaced or changed by data transmitted from the external unit via the telemetry means. In this way, after implantation of the implantable system, the operating software as such can be changed or even completely replaced, as is explained for otherwise known systems for rehabilitation of hearing disorders in commonly owned U.S. Pat. No. 6,198,971 which is hereby incorporated by reference.

In addition, the design of totally implantable systems preferably is accomplished in a manner known per se, such that after implantation, operating parameters, i.e. patient-specific data, for example audiological adaption data, or variable implant system parameters (for example, a variable in a software program for control of battery recharging), can be transmitted transcutaneously, i.e., wirelessly through the closed skin, to the implant and can thus be changed. In such a case, the software modules are designed to be preferably dynamic, or in other words, adaptive, in order to approach as optimally as possible the formation of a traveling wave configuration which approximates the type of traveling wave formation of a healthy, undamaged inner ear. In particular, the software modules can be designed to be adaptive, and parameter matching can be done by training conducted by the implant wearer and using other aids.

Furthermore, the signal processing electronics can contain a software module which achieves simulation of a "healthy" cochlear amplifier as optimally as possible based on an adaptive neural network. In this case, also, training of this neural network can be conducted by the implant wearer and/or using other external aids. Especially in the neural network for simulation of a "healthy" cochlear amplifier, the principle of time-reversed acoustics (TRA) can be implemented, and control of the output-side electromechanical transducers can take place by TRA such that locally limited areas of the cochlea are mechanically stimulated.

The storage arrangement for storage of operating parameters and the storage arrangement for storage and retrieval of the operating program can be implemented as storages independent of one another; however, there can also be a single storage in which both operating parameters and also operating programs can be stored.

The latter approach allows matching of the system to circumstances which can be detected only after implantation of the implantable system. Thus, for example, in an at least partially implantable hearing system for rehabilitation of a monaural or binaural inner ear disorder and of a tinnitus by mechanical stimulation of the inner ear, the sensoric (acoustic sensor or microphone) and actoric (output stimulator) biological interfaces are always dependent on anatomic, biological and neurophysiological circumstances, for example on the interindividual healing process. These interface parameters can be individual, also especially time-variant. Thus, for example the transmission behavior of an implanted microphone can vary interindividually and individually in view of the extent of covering by tissue, and the transmission behavior of an electromechanical transducer which is coupled to the inner ear can vary in view of different coupling qualities. Such differences of interface parameters which cannot be eliminated or reduced in the devices known from the prior art even by replacing the implant can now be optimized by changing or improving the signal processing of the implant.

In an at least partially implantable hearing system it can be advisable or become necessary to implement signal processing algorithms which have been improved after implantation as follows:

speech analysis processes (for example, optimization of a fast Fourier transform (FFT))

static or adaptive noise detection processes static or adaptive noise suppression processes processes for optimization of the signal to noise ratio within the system optimized signal processing strategies in progressive hearing disorder output level-limiting processes for protection of the patient in case of implant malfunctions or external faulty programming processes of preprocessing of several sensor (microphone) signals, especially for binaural positioning of the sensors processes for binaural processing of two or more sensor signals in binaural sensor positioning, for example optimization of spacial hearing or spacial orientation phase or group delay time optimization in binaural signal processing processes for optimized driving of the output stimulators, especially for binaural positioning of the stimulators Among others, the following signal processing algorithms can be implemented with this system even after implantation:

processes for feedback suppression or reduction processes for optimization of the operating behavior of the output transducer(s) (for example, optimization of the frequency response and phase response, and improvement of the impulse response)

speech signal compression processes for sensorineural hearing loss signal processing methods for recruitment compensation in sensorineural hearing loss Furthermore, in implant systems with a secondary power supply unit, i.e. a rechargeable battery system, but also in systems with a primary battery supply, it can be assumed that these electrical power storages will enable longer and longer service lives and thus increasing residence times in the patients as technology advances. It can be assumed that fundamental and applied research for signal processing algorithms will make rapid progress. The necessity or the patent desire for operating software adaptation and modification will therefore presumably take place before the service life of the implanted power source expires. The system described here allows this adaptation of the operating programs of the implant even when the implant has already been implanted.

Preferably, there can furthermore be provided a buffer storage arrangement in which data transmitted from the external unit via the telemetry means can be buffered before being relayed to the signal processor. In this way, the transmission process from the external unit to the implanted system can be terminated before the data transmitted via the telemetry means are relayed to the signal processor.

Furthermore, there can be provided checking logic which checks the data stored in the buffer storage arrangement before relaying the data to the signal processor. There can be provided a microprocessor module, especially a microcontroller, for control of the A/D-converters and/or the D/A converters and/or the signal processor within the implant via a data bus, preferably the checking logic and the buffer storage arrangement being implemented in the microprocessor module, and wherein also program parts or entire software modules can be transferred via the data bus and the telemetry means between the outside world, the microprocessor module and the signal processor.

An implantable storage arrangement for storing the working program for the microprocessor module is preferably assigned to the microprocessor module, and at least parts of the working program for the microprocessor module can be changed or replaced by data transmitted from the external unit via the telemetry means.

In another embodiment of the invention, at least two storage areas for storage and retrieval of at least the operating program of the signal processor may be provided. This contributes to the reliability of the system, in that due to the multiple presence of a storage area which contains the operating program(s), for example, after transmission from the exterior or when the implant is turned on, checking for the absence of faults in the software can be done.

Analogously to the above, the buffer storage arrangement can also comprise two storage areas for storage and retrieval of data transferred from the external unit via the telemetry means, so that after data transmission from the external unit still in the area of the buffer storage, the absence of errors in the transferred data can be checked. The storage areas can be designed, for example, for complementary filing of the data transferred from the external unit. At least one of the storage areas of the buffer storage arrangement, however, can also be designed to store only part of the data transferred from the external unit, wherein, in this case, the absence of errors in the transferred data is checked in sections.

Furthermore, to ensure that, in case of transmission errors, a new transmission process can be started, a preprogrammed read-only memory (ROM) area which cannot be overwritten can be assigned to the signal processor, in which ROM area the instructions and parameters necessary for "minimum operation" of the system are stored, for example, instructions which after a "system crash" ensure at least error-free operation of the telemetry means for receiving an operating program and instructions for its storage in the control logic.

As already mentioned, the telemetry means is advantageously designed not only for reception of operating programs from the external unit but also for transfer of operating parameters between the implantable part of the system and the external unit such that, on the one hand, such parameters (for example the volume) can be adjusted by a physician, a hearing aid acoustics specialist or the wearer of the system himself, and, on the other hand, the system can also transfer the parameters to the external unit, for example to check the status of the system.

A totally implantable hearing system of the aforementioned type can have on the implant side, in addition to the actoric stimulation arrangement and the signal processing unit, at least one implantable acoustic sensor and a rechargeable electrical storage element, and, in this case, a wireless transcutaneous charging device can be provided for charging of the storage element. For a power supply, there can also be provided a primary cell or another power supply unit which does not require transcutaneous recharging. This applies especially when it is considered that in the near future, mainly by continuing development of processor technology, a major reduction in power consumption for electronic signal processing can be expected so that, for implantable hearing systems, new forms of power supply will become usable in practice, for example a power supply which uses the Seebeck effect, as is described in U.S. Pat. No. 6,131,581. Preferably, there is also provided a wireless remote control for control of the implant functions by the implant wearer.

For partially implantable hearing systems, at least one acoustic sensor, an electronic arrangement for audio signal processing and amplification, a power supply unit and a modulator/transmitter unit are contained in an external module which can be worn outside on the body, especially on the head over the implant. The implant has an intracochlear or extracochlear transducer array, but is passive in terms of energy and receives its operating energy and transducer control data via the modulator/transmitter unit in the external module.

The described system can be designed to be monaural or binaural. A binaural system for rehabilitation of a hearing disorder of both ears has two system units which each are assigned to one of the two ears. In doing so, the two system units can be essentially identical to one another. However, one of the system units can also be designed as a master unit and the other system unit as a slave unit which is controlled by the master unit. The signal processing modules of the two system units can communicate with one another in any way, especially via a wired implantable line connection or via a wireless connection, preferably a bidirectional high frequency path, an ultrasonic path coupled by bone conduction, or a data transmission path which uses the electrical conductivity of the tissue of the implant wearer such that in both system units optimized binaural signal processing and transducer array control are achieved.

The electromechanical transducers can be made as hollow bodies which, when a voltage signal is applied, undergo a dynamic volume change and from which intracochlear fluid which is located in the transducer cavity is pressed out, wherein the electromechanical transducers designed in this manner can be housed in a hose-shaped carrier which is provided with at least one opening for passage of intracochlear fluid adjacent to at least one end of the transducers.

These and further objects, features and advantages of the present invention will become apparent from the following description when taken in connection with the accompanying drawings which, for purposes of illustration only, shows several embodiments in accordance with the present invention.

BRIEF DESCRIPTION OF THE DRAWINGS

FIG. 1 schematically shows an embodiment of an intracochlear electromechanical transducer array, FIG. 2 shows a a dynamic change of volume or surface as a detail of FIG. 1, FIG. 3 schematically shows an embodiment of an electromechanical transducer array which is to be applied extracochlearly, FIG. 4 schematically shows an embodiment of the structure of the extracochlear electromechanical transducer array as shown in FIG. 3, FIG. 5 schematically shows an embodiment of the structure of a signal processing electronic module of an at least partially implantable hearing system, FIG. 6 schematically shows an embodiment of the structure of a totally implantable hearing system with an intracochlear transducer array as shown in FIG. 1, FIG. 7 schematically shows an embodiment of the structure of a totally implantable hearing system with an extracochlear transducer array as shown in FIG. 4, FIG. 8 schematically shows an embodiment of the structure of a partially implantable hearing system with an intracochlear transducer array as shown in FIG. 1.

DETAILED DESCRIPTION OF THE INVENTION

Figure 13:
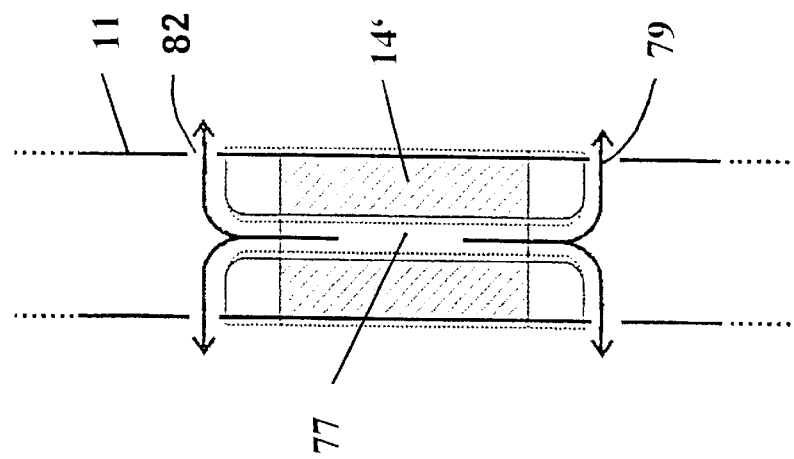
FIG. 13 shows an embodiment of an electromechanical transducer which corresponds to that of FIG. 2 except that the transducer embedded in the carrier is designed as a hollow cylinder.

The intracochlear electromechanical transducer array which is shown in FIG. 1 and which is labeled 10 as a whole, is designed similar to a multichannel intracochlear cochlea implant electrode arrangement. The intracochlear electromechanical transducer array 10 has a mechanical carrier 11 which is preferably formed of a flexible molded part of preferably circular cross section. The molded part is advanced into the inner ear through an artificial opening of the cochlea 12 or the round window. Instead of an array of electrical stimulation electrodes of a cochlear implant electrode arrangement, here there are several output-side electromechanical transducers 14 along the carrier 11 which are shown schematically in FIG. 1 as cylindrical elements with a circular cross section. Within the carrier 11 there are electrical lines (not shown) leading to the transducers 14.

The transducers 14 preferably operate according to the principle of dynamic volume change as a result of dynamic surface enlargement or reduction according to a controlling electrical transducer AC voltage signal. Such a dynamic change of volume or surface is shown schematically in FIG. 2. In FIG. 2, the broken lines 15 and 16 show the minimum and the maximum volume, respectively. The required volume changes for a suitable equivalent acoustic pressure level of about 100 dB SPL amount to about $2 \times 10^{-4}$ microliters (U.S. Pat. No. 5,772,575).

The transducers 14 are, for example, distributed equidistantly along the carrier 11 or at logarithmic distances according to the tonotopic location-frequency assignment along the basilar membrane of the inner ear. The total diameter of the transducer array arrangement 10 is preferably in the range of from 0.4 mm (apical area 18 as shown in FIG. 1) to 2.0 mm (basal area 19 as shown in FIG. 1). The total length of the transducer array 10 is preferably between 5 mm and 50 mm. The transducer elements 14 are preferably embedded in the carrier 11 for reasons of biocompatibility such that they are completely surrounded by a thin layer of carrier material (not shown in FIG. 1). The carrier 11 of the transducer array 10 composed of a biocompatible material which is bio-stable in the inner ear, preferably polymers, such as suitable silicones. Between the individual transducers 14, mechanical attenuation elements 20 can be embedded in the carrier 11; they minimize the mechanical wave propagation within the carrier to adjacent transducer elements. When the cross sectional geometry of the attenuation elements 20 is similar to that of the carrier 11, the material of the attenuation elements 20 is preferably chosen such that there is a high mechanical impedance difference relative to the carrier material in order to achieve high attenuation values.

Figure 3:
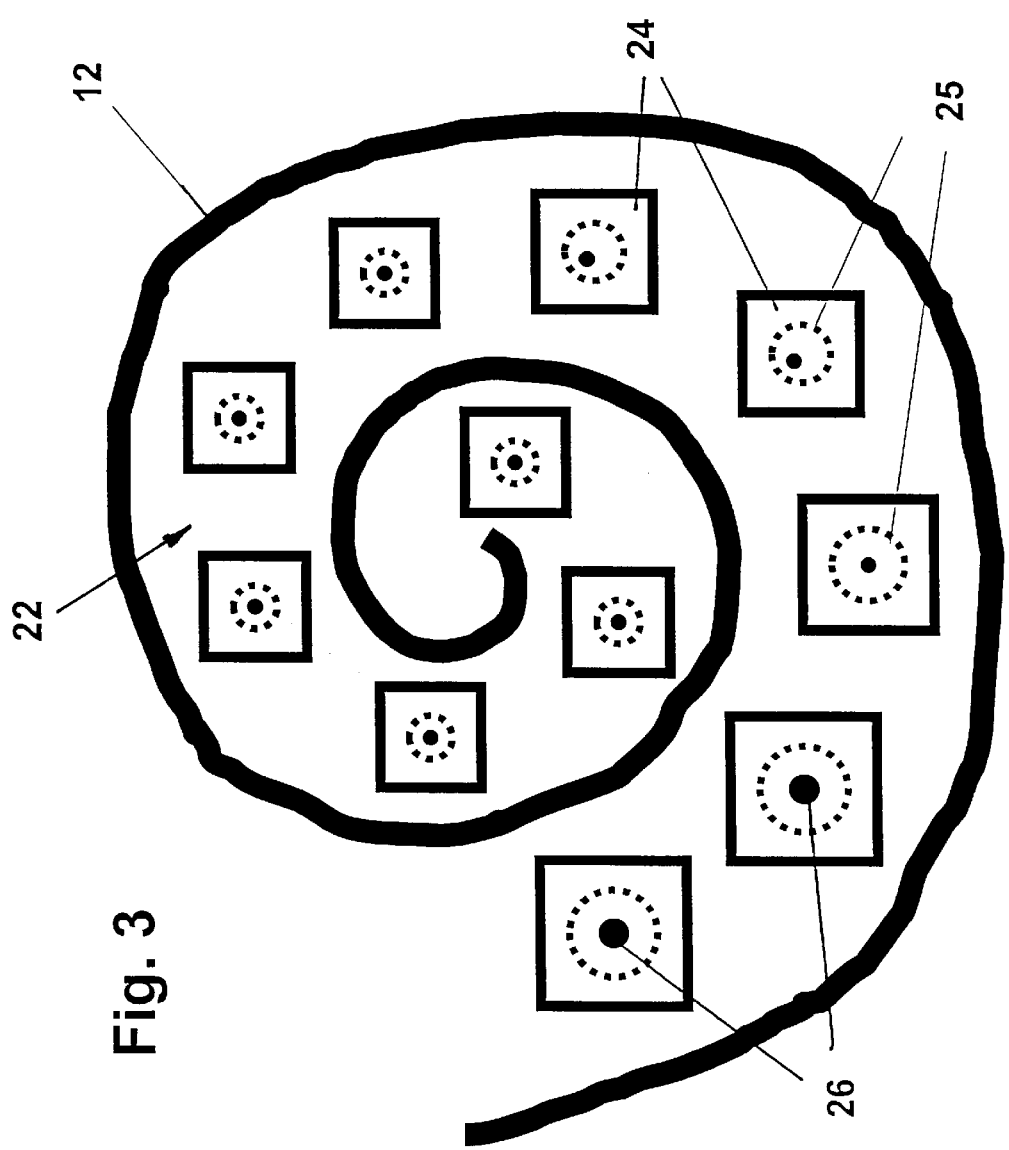

FIG. 3 schematically shows an electromechanical transducer array 22 which is to be applied extracochlearly. Here, several miniaturized output-side electromechanical transducers 24 are placed over openings or holes (cochleostomia) 25 made in the bony wall which borders the cochlea 12 such that coupling elements 26 attached on the transducer-output side project through the cochlear openings 25 into the lymphatic inner ear spaces. Mechanical stimuli of the transducers 24 are produced intracochlearly as volume displacements which lead to a hearing impression. The bony cochlea border area to be provided with holes 25 is surgically accessible from the mastoid in the area of the promontory.

The transducers 14, 24 can operate according to any known electromechanical transducer principle, specifically the electromagnetic, electrodynamic, piezoelectric, magnetostrictive or dielectric (capacitive) principle. In particular, for the extracochlear array embodiment, the piezoelectric principle and the dielectric or capacitive principle are particularly preferred. Preferably, the extracochlear transducer array 22, but optionally at least in part also the intracochlear transducer array 10, are developed and produced using methods of Microsystems engineering which allow high miniaturization and excellent reproducibility of the individual transducers 24 on an array. These properties of production using microsystems engineering can be especially advantageous because, as expected in the intended function of the array, the phase synchronism of the individual transducers is very important. One possible Microsystems engineering structure of an individual transducer is given in the patent literature by Ron Maynard (WO-A-99/03146).

The individual electromechanical transducers 14, 24 are controlled by an electronic preprocessing system which is explained detail below such that, by the respective choice of the spectral transmission range per transducer, the vibratory amplitude and the phase angle of the transducers with respect to one another, and as a result of the overall inner ear actoric stimulation, a traveling wave is formed on the basilar membrane such that the traveling wave, for the respective external sound event, is as similar as possible to the traveling wave form which would result in case of an undamaged cochlear amplifier and thus intact outer hair cells.

Figure 4:
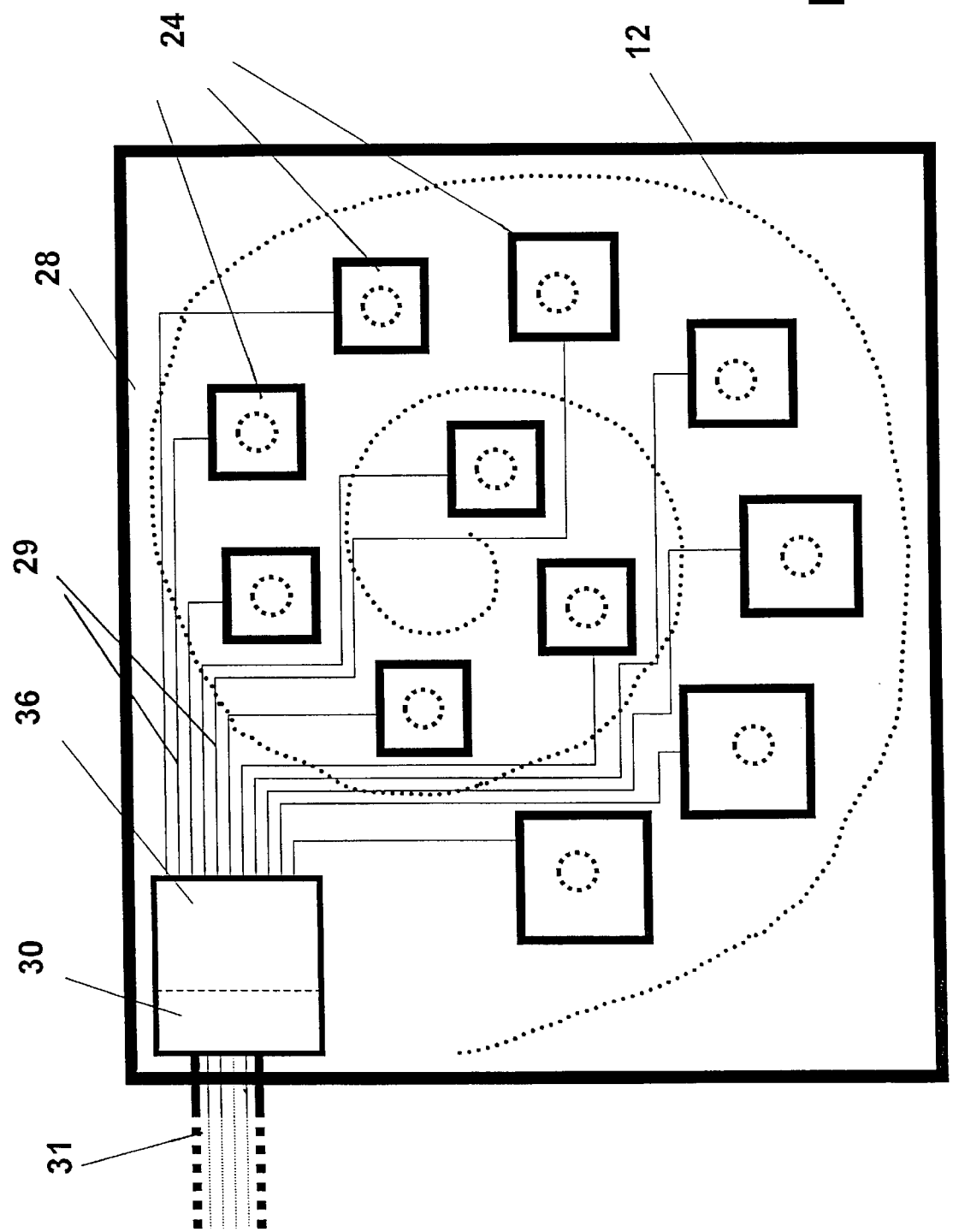

FIG. 4 schematically shows a possible structure of the extracochlear electromechanical transducer array 22 as shown in FIG. 3 which can be produced preferably using methods of Microsystems engineering. On a carrier plate (substrate) 28, there are several transducer units 24 (for example, in accordance with International Patent Application Publication WO-A-99/03146) distributed geometrically so as to correspond to the statistical average of the geometrical cochlear dimensions (the contour of the cochlea 12 is shown with a dotted-line). This substrate 28 also contains the electrical transducer lines 29 (indicated in FIG. 4). Furthermore, there is an electrical terminal panel 30 which is produced at the same time using Microsystems engineering and which enables proper connection of a multipole, biocompatible implant lead 31 to the electronic module 34 which is illustrated in FIGS. 6 to 10 and which contains the driving signal processing electronics of the implantable hearing system. In addition, the substrate 28 can contain an electronic module 34 which is produced at the same time using Microsystems engineering and which, for example, can contain the driver stages which control the transducers 24.

Advantageously, this module 34 can also contain decoding logic and transducer components which enable connection of a minimum pole implant lead. Thus, for example, the array connector can consist of only three lines (ground, data and clock signal), and the necessary supply of electrical operating energy can take place by phantom feed on the clock signal line or by rectifying the clock signal directly. The transducer-driving signals are then in digitally encoded form and are transmitted serially with a high clock rate. Furthermore, an interface module can be provided which enables digital data transmission via the implant lead, advantageously by means of an optical fiber. For serial data transmission, the corresponding D/A converters and driver modules assigned to the transducers 24 are contained in the electronic module 36. The entire transducer array 22 including the carrier structure (substrate) 28 is equipped with biocompatible coating which, for example, preferably is made of polymers known from implant technology (polytetrafluoroethylene, polyurethane, silicones).

Figure 5:
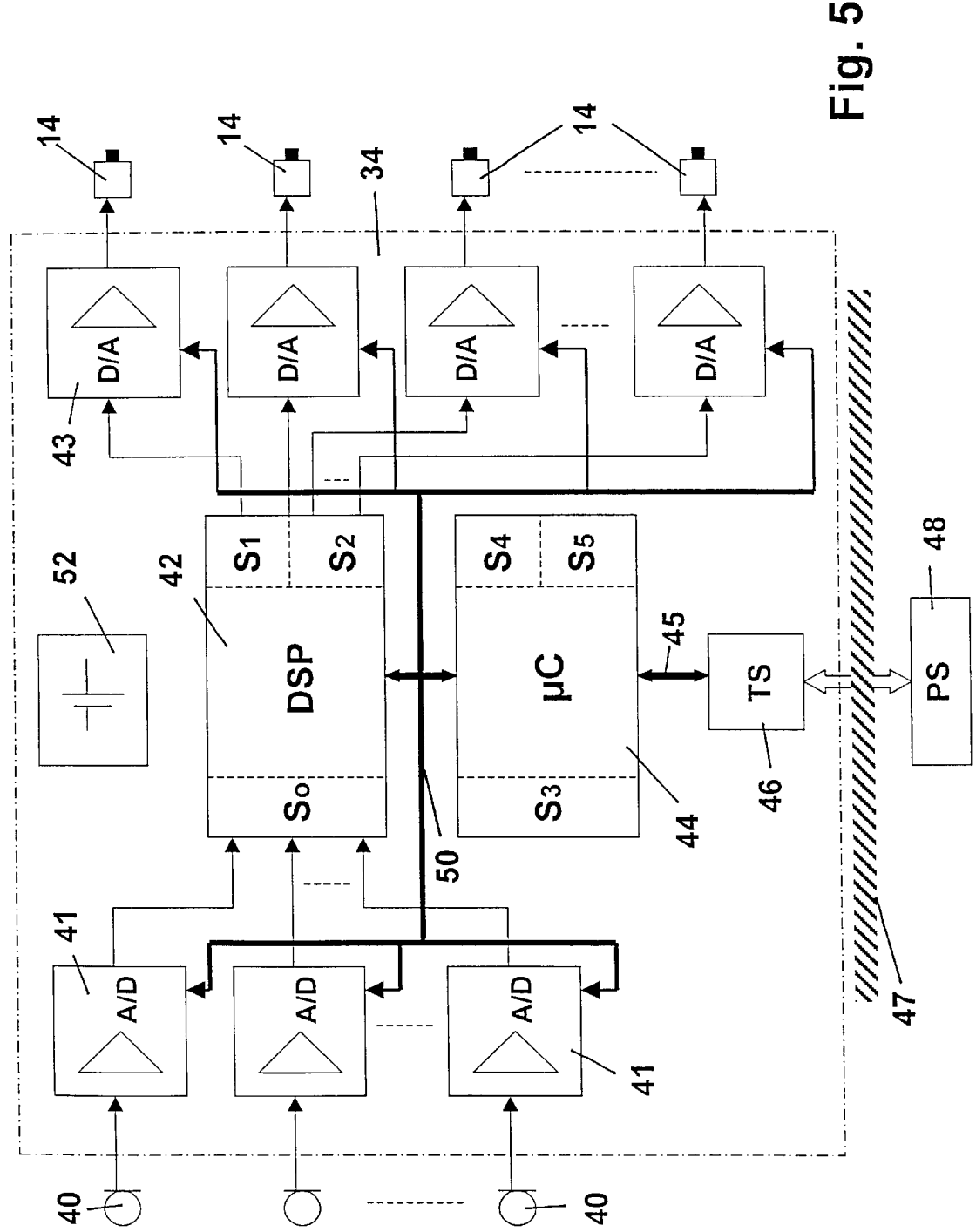

FIG. 5 shows a possible structure of the signal processing electronic module 34 of an at least partially implantable hearing system. The external acoustic signal is picked up via one or more acoustic sensors (microphones) 40 and is converted into electrical signals. The analog electrical sensor signals are routed to modules 41 in which they are preprocessed, especially preamplified, and converted into digital signals (A/D). This preprocessing can be comprised of, for example, analog linear or nonlinear preamplification and filtering (for example, antialiasing filtering).

The digitized sensor signals are further processed in a digital signal processor (DSP) 42. The signal processor 42 contains a read-only-memory area $S_0$ which cannot be overwritten and in which the instructions and parameters necessary for "minimum operation" of the system are stored, and storage areas $S_1$ and $S_2$ in which the operating software of the intended function or functions of the implant system are stored. The rewriteable program storages $S_1$ and $S_2$ for storing the operating software can be based on EEPROM or on static RAM cells, and, in the latter case, provisions should be made for this RAM area to always be "buffered" by the power supply system within the implant.

The digital output signals of the signal processor 42 are converted in a digital-analog converter (D/A) 43 into analog signals and are amplified and then supplied to the output side electromechanical transducers 14. The D/A converters 43 can optionally be omitted, if, for example, in a hearing system with an electromagnetic output transducer, for example, a pulse-width modulated, serial digital output signal of the signal processor 42 is transferred directly to the output transducer 14.

The signal processor 42 executes the intended function of the hearing implant. This includes audio signal processing for rehabilitation of a hearing disorder and optionally also signal generation, in the case of a system with additional tinnitus masking or noiser functions. Furthermore, the digital signal processor 42 contains software modules which control the output-side electromechanical transducers 14 such that the spectral, time, amplitude- and phase-referenced transducer signal properties are dimensioned such that a traveling wave is produced on the basilar membrane of the damaged inner ear such that the traveling wave is as similar as possible to that of healthy hearing. These software modules can be designed to be static or dynamic. A static design is intended to mean that the software modules, based on scientific findings, are stored once in the program storage of the signal processor 42 and remain unchanged. Dynamic means that these software modules are "able to learn," in order to approach as optimally as possible the desired traveling wave configuration in a time iterative manner. This means that the software modules can be designed to be adaptive, and parameter matching is done by training conducted by the implant wearer and optionally using other aids such as rehabilitation programs. Furthermore, a software module can be provided which approximates simulation of a "healthy" cochlear amplifier as optimally as possible based on an adaptive neural network. Training of this neural network can take place again by the implant wearer and/or by using other external aids.

A method to simulate a "healthy" cochlear amplifier as optimally as possible can be the implementation of the principle of "Time-Reversed Acoustics" (TRA) (M. Fink: "Time-Reversed Acoustics" Scientific American 281:5 (1999), pp. 67–73). Control of the output-side transducer elements 14 takes place by TRA such that locally limited areas of the cochlea are mechanically stimulated. While in conventional applications of TRA the registration of the distributed sound event and the transmission of the time-reversed signal take place in the same preparation, these two steps are separated in the present case. For example, the distributed events can be determined intracochlearly in a suitable animal model; in the present application of a hearing system for human use the time-reversed stimuli then are applied, optionally with parameter matching to the altered geometry of the human cochlea.

The system as shown in FIG. 5 contains a further microprocessor module, for example, a microcontroller ($\mu$C) 44 with the associated storages ($S_3$, $S_4$, $S_5$), in order to permit the described, software-based algorithms for as optimum as possible simulation of the cochlear amplifier to be implemented also postoperatively, especially in a total implant. The storage $S_3$ is a rewriteable storage in which an operating program for the microcontroller 44 is stored. Especially the operating software portions of the implant management system (for example, administration, monitoring and telemetry functions) can be stored in the storage areas $S_4$ and $S_5$. Storages $S_1$ and/or $S_2$ and/or $S_4$ and/or $S_5$ can also store patient-specific data, for example audiological adaptation parameters which can be altered from the outside.

On the one hand, the microcontroller 44 communicates via a bidirectional data bus 45 and a telemetry system (TS) 46 wirelessly (for example, via inductive coupling) through the closed skin indicated at 47 with an external programming system (PS) 48. The programming system 48 can be a PC-based system with corresponding programming, processing, display and administration software. Via this telemetry interface, the operating software of the implant system which is to be changed or completely replaced is transmitted and at first buffered in the storage area $S_4$ and/or $S_5$ of the microcontroller 44. Thus, for example, simple verification of software transmission can be done by a reading process via the telemetry interface before the operating software or the corresponding signal processing portions of this software are transmitted into the program storage areas $S_1$ and $S_2$ of the digital signal processor 42 via a data bus 50.

Furthermore, the operating program for the microcontroller 44 can be changed or replaced in whole or in part via the telemetry interface using the external programming system 48.

On the other hand, the microcontroller 44 controls, via the bidirectional data bus 50, the A/D-converters 51 of the sensor preprocessing unit, the D/A converters 43 for controlling the output-side electromechanical transducers 14 and the signal processor 2 itself within the implant. Via the data bus 50, program parts or entire software modules are also transmitted between the outside world, the microcontroller 44 and the signal processor 42.

In the totally implanted embodiment, the implant system also contains a primary or secondary battery cell 52 which supplies the individual modules with electrical operating energy.

Figure 6:
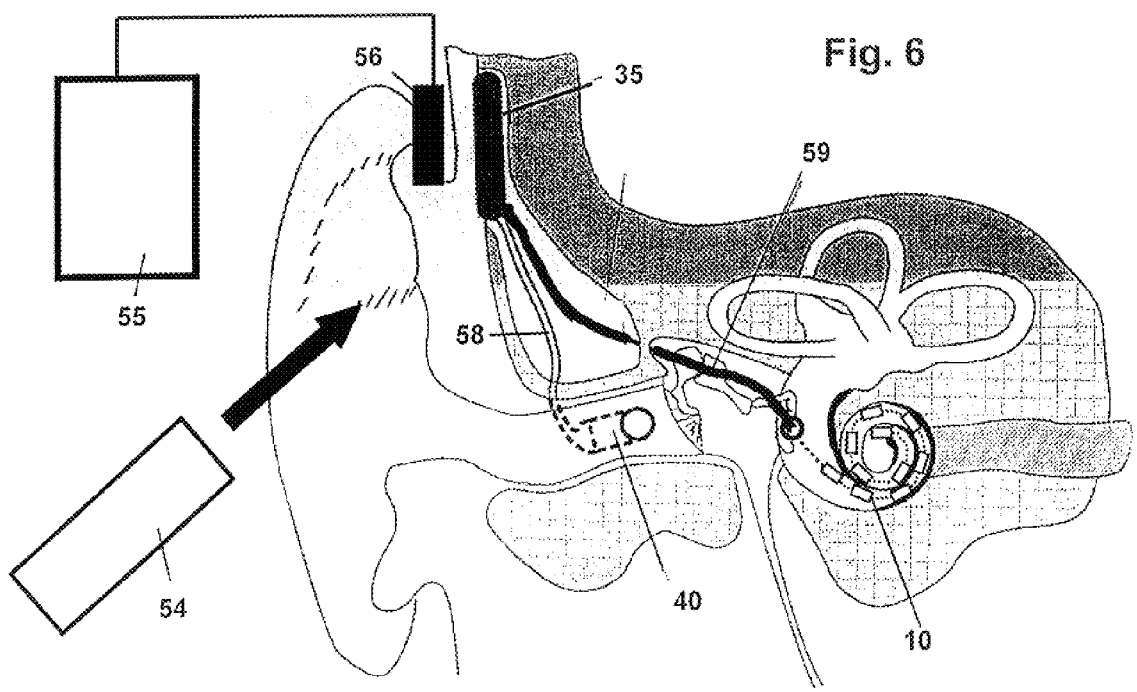

FIG. 6 schematically shows the structure of a completely implantable hearing system with an intracochlear transducer array 10 as shown in FIG. 1 and an implantable microphone 40. A wireless remote control 54 is used to control the implant functions by the implant wearer. Furthermore, there is a charging system comprising a charging device 55 for wireless transcutaneous recharging of a secondary battery located in the implant for power supply of the hearing system, for example, of the battery 52 in FIG. 5.

The microphone 40 can advantageously be built in the manner known from commonly owned U.S. Pat. No. 5,814, 095, which is hereby incorporated by reference. The microphone 40 can be provided with a microphone capsule which is hermetically sealed on all sides within a housing, and with an electrical lead-in wire connector for routing at least one electrical connection from within the housing to the outside thereof, wherein the housing has at least two legs, which are arranged at an angle relative to one another, a first of said legs containing the microphone capsule and being provided with a sound inlet membrane, and a second of said legs containing the electrical lead-in wire connector and being set back relative to the plane of the sound inlet membrane, and wherein the geometry of the microphone housing is chosen such that, when the microphone is implanted in the mastoid cavity, the leg which contains the sound inlet membrane projects from the mastoid into an artificial hole in the posterior bony wall of the auditory canal and the sound inlet membrane touches the skin of the wall of the auditory canal.

To affix the microphone 40, there can preferably be a fixation element of the type known from U.S. Pat. No. 5,999,632 which has a sleeve, a cylindrical housing part of which surrounds the leg which contains the sound inlet membrane, wherein the sleeve is provided with projecting, elastic flange parts which can be placed against the side of the wall of the auditory canal facing the skin of the auditory canal. The fixation element preferably comprises a holding device which, before implantation, maintains the flange parts mentioned above, against the elastic restoration force of the flange parts, in a bent position which allows insertion through the hole of the wall of the auditory canal.

The charging system also includes a charging coil 56 which is connected to the output of the charging device 55 and which preferably, in the manner known from U.S. Pat. No. 5,279,292, forms part of a transmitting serial resonant circuit which can be inductively coupled to a receiving serial resonant circuit (not shown). In the embodiment shown in FIG. 6, the receiving serial resonant circuit can be part of the electronic module 34 and, according to U.S. Pat. No. 5,279, 292, can form a constant current source for the battery 52 (FIG. 5). In this case, the receiving serial resonant circuit is connected in a battery charging circuit which, depending on the respective phase of the charging current flowing in the charging circuit, is closed via one or another branch of a full wave rectifier bridge.

In the arrangement shown in FIG. 6, the electronic module 34 is connected via a microphone line 58 to the microphone 40 and via a transducer array line 59 to the intracochlear transducer array 10.

Figure 7:
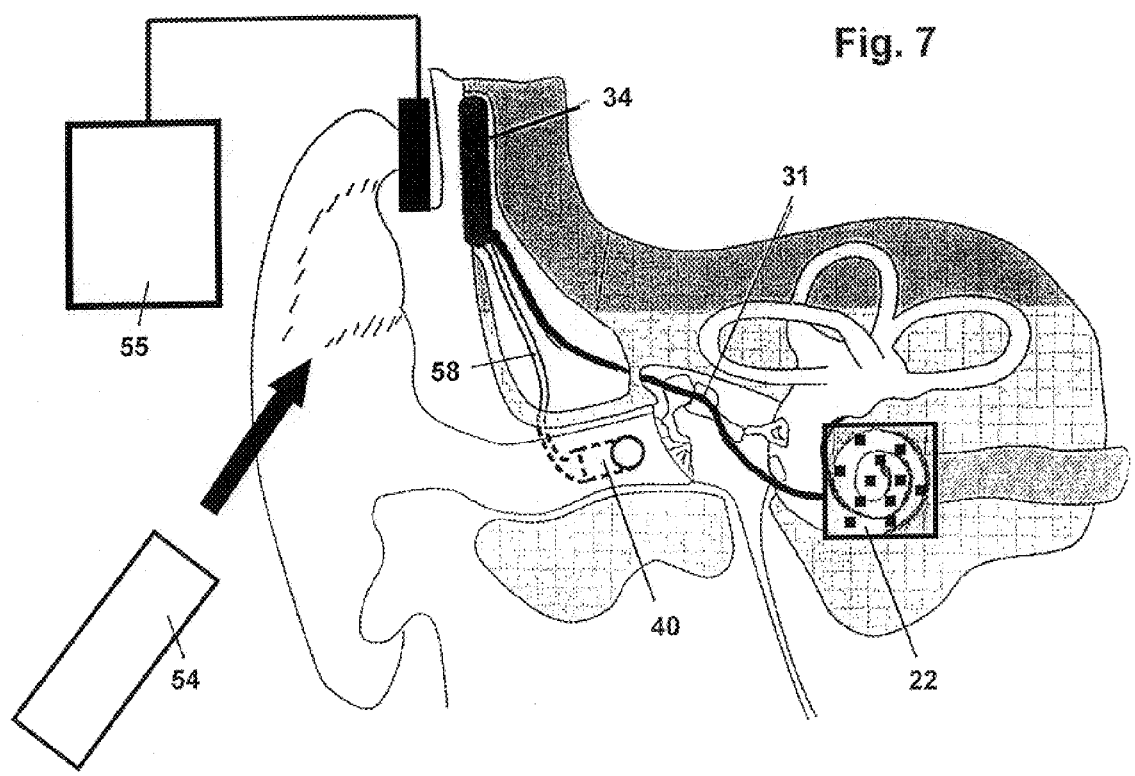

FIG. 7 schematically shows the structure of a totally implantable hearing system comprising an extracochlear transducer array 22 as shown in FIGS. 3 and 4 and the implantable microphone 40. In this case, as above, the wireless remote control 54 is provided for controlling the implant functions by the implant wearer, and a charging system, comprising the charging device 55 and the charging coil 56 as shown in FIG. 6, is used for wireless transcutaneous recharging of the secondary battery 52 (FIG. 5) which is located in the implant for power supply of the hearing system. The transducer array 22 is connected to the electronic module 34 via the implant lead 31.

Figure 8:
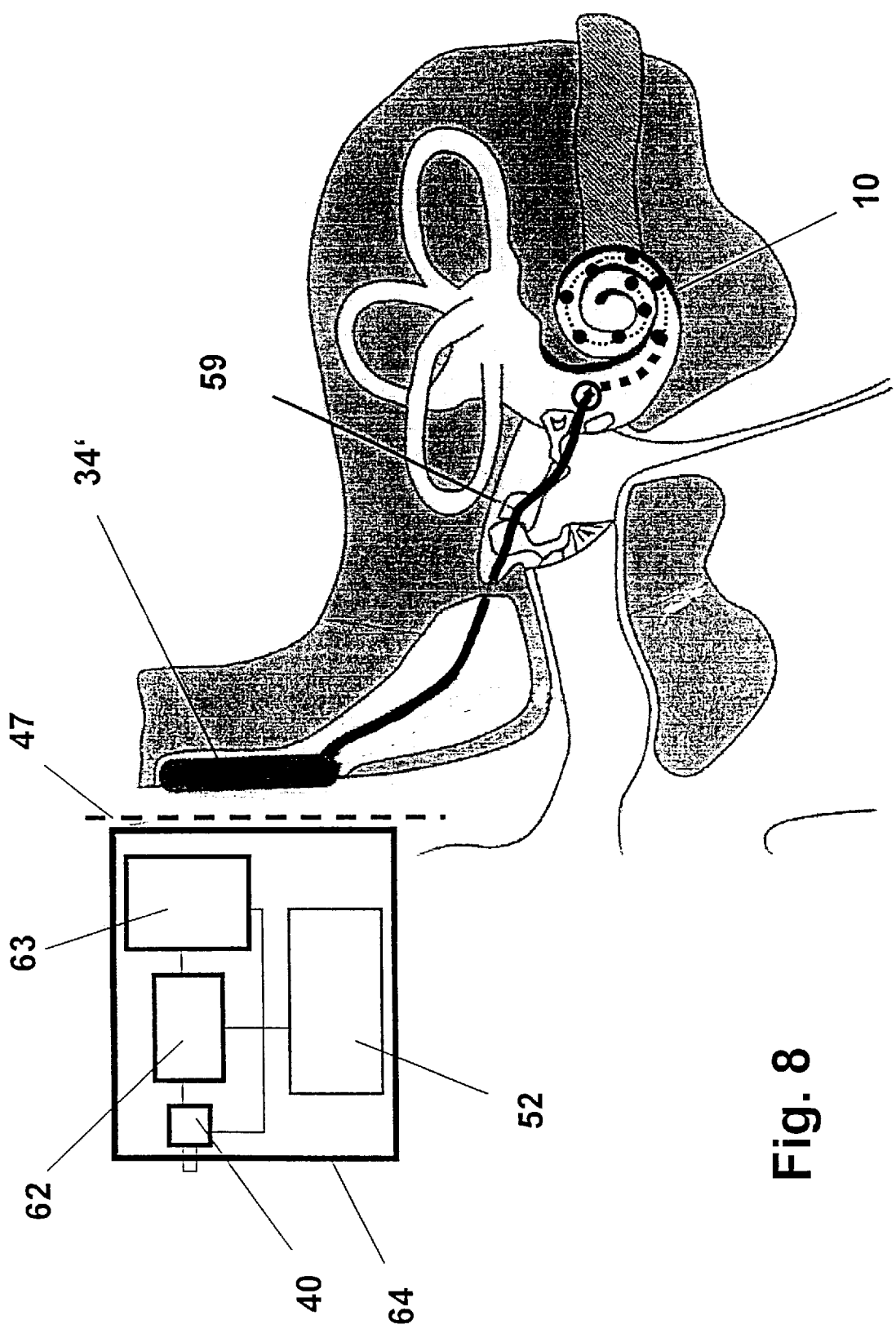

FIG. 8 schematically shows the structure of a partially implantable hearing system comprising an intracochlear transducer array 10 as shown in FIG. 1. This partially implantable system contains a microphone 40, an electronic module 62 for electronic signal processing similar to that of FIG. 5 (but without the telemetry system 46), a power supply 52 and a modulator/transmitter unit 63 in an external module 64 which is to be worn externally on the body, preferably on the head over the implant. As in known partial implants, the implant is passive in terms of energy. Its electronic module 34' (without the battery 52) receives its operating energy and transducer control data via the modulator/transmitter unit 63 in the external part 64. In such a partially implantable hearing system, the transducer array can also be made extracochlearly as shown in FIGS. 3 and 4.

Figure 9:
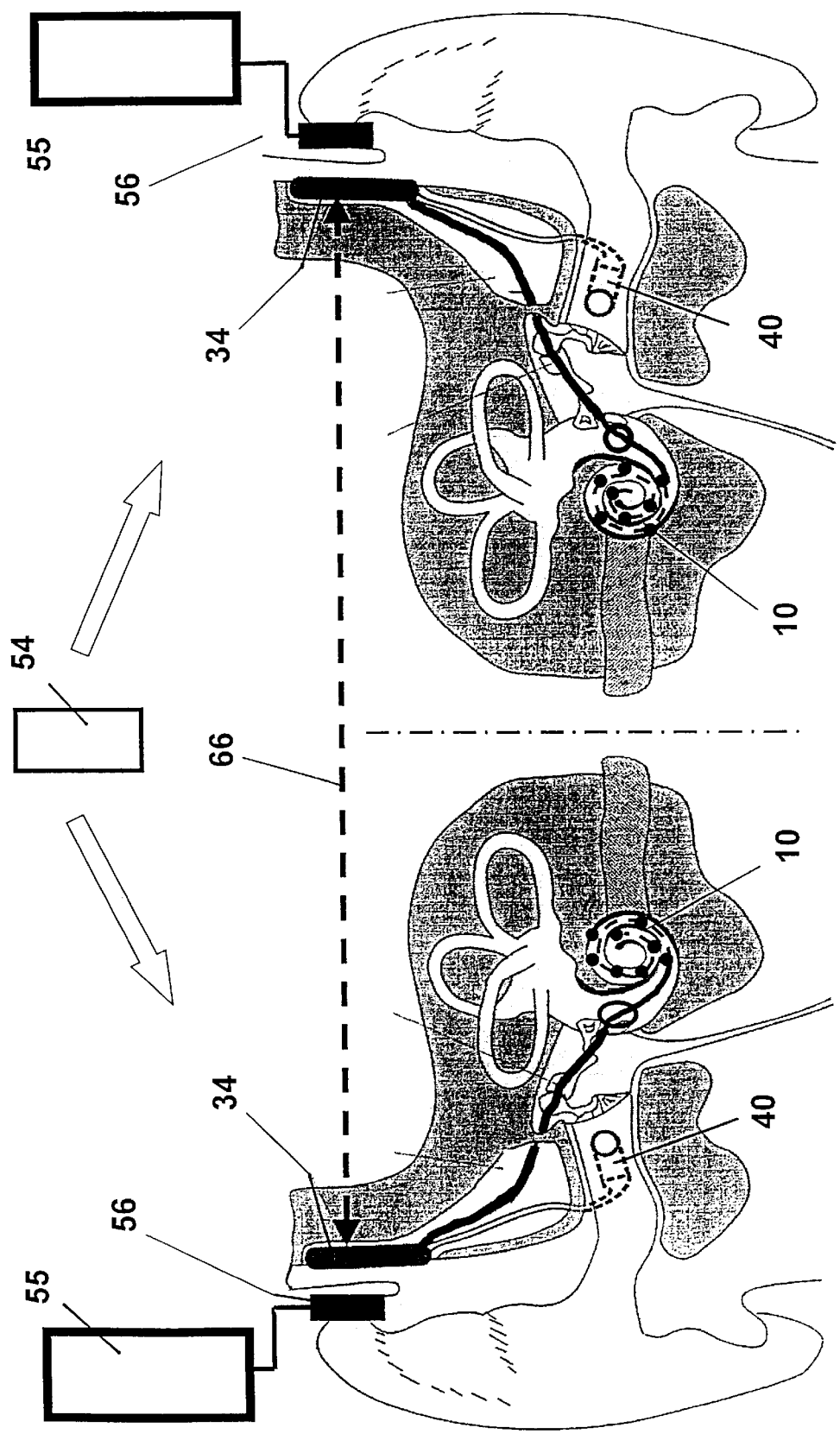
FIG. 9 shows a binaural application of a hearing implant as shown in FIG. 6 in which the signal processing modules communicate with one another via a wired implantable line connection.
Figure 10:
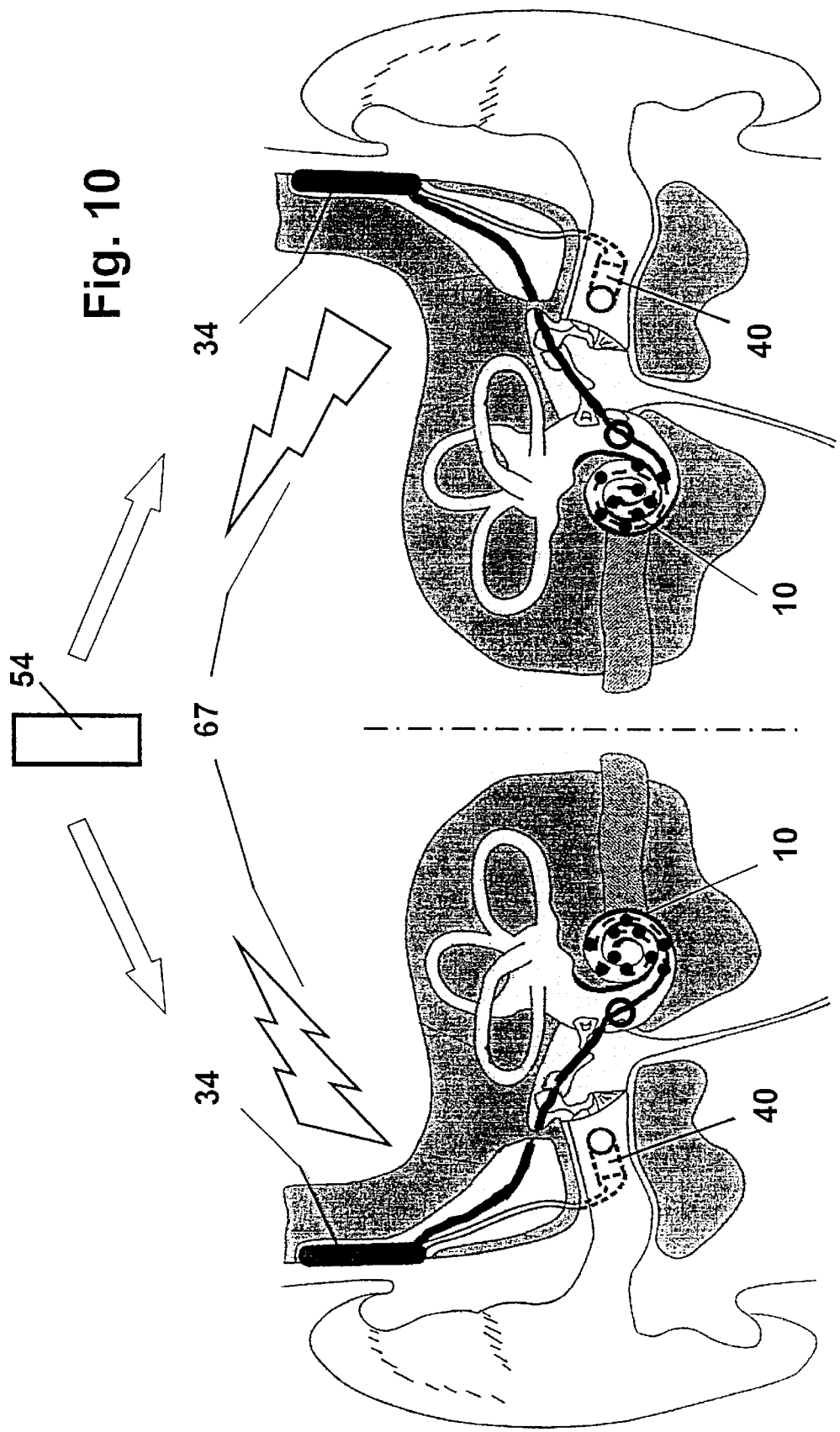
FIG. 10 shows a binaural application of a hearing implant as shown in FIG. 6 in which the signal processing modules communicate with one another via a wireless connection.

FIG. 9 shows a binaural application of a hearing implant (in this case provided with intracochlear transducer arrays 10) in which the signal processing modules 34 communicate with one another via a wired implantable line connection 66 such that optimum binaural signal processing and transducer array control is attained in both inner ears provided with implants. Furthermore, in this case, as above, transcutaneous charging devices 55 and coils 56 are provided if secondary energy storage elements (batteries 52) are included in the implants. Also included is a wireless remote control 54 for use by the implant wearer which synchronously controls the two electronic modules 34. FIG. 10 shows the binaural application of a hearing implant (in this case provided with intracochlear transducer arrays 10) in which the signal processing modules 34 communicate with one another via a wireless connection (for example, a bidirectional high frequency path indicated at 67) such that optimum binaural signal processing and transducer array control is achieved in both inner ears provided with implants. Furthermore, in this case, as above, transcutaneous charging devices 55 and coils 56 (not shown) are provided if secondary energy storage elements (batteries 52) are included in the implants. Also included is a wireless remote control 54 for use by the implant wearer which synchronously controls the two electronic modules 34.

Figure 11:
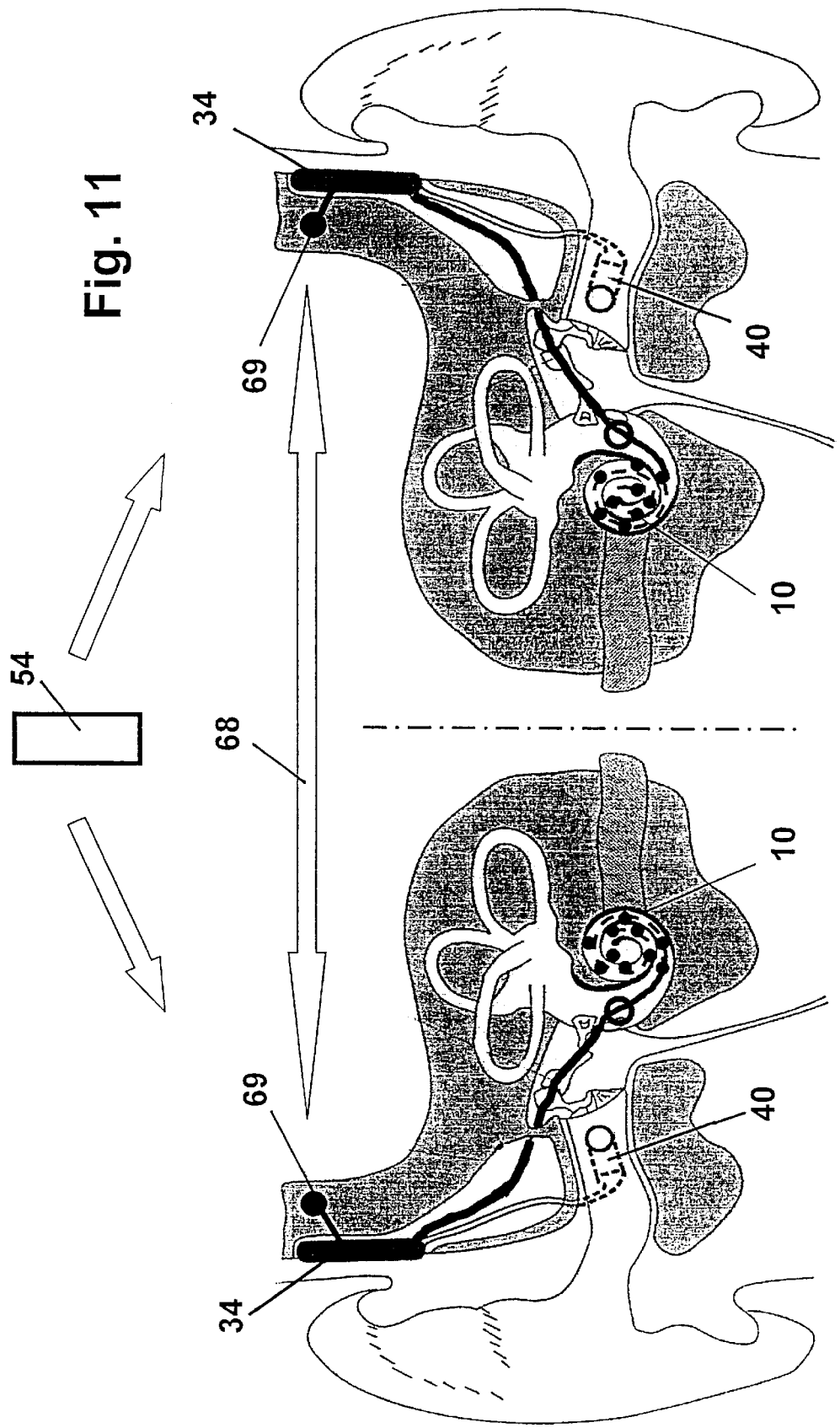
FIG. 11 shows a binaural application of a hearing implant as shown in FIG. 6 in which the signal processing modules communicate with one another via a ultrasonic path coupled by bone conduction.

The binaural embodiment of the hearing implant shown in FIG. 11 differs from that of FIG. 10 only in that, for wireless communication between the signal processing modules 34 of the two system units, there is an ultrasonic path 68 including ultrasonic couplers 69 which are coupled by bone conduction. In this case, the bidirectional information, for example digital, is preferably amplitude modulated or frequency modulated onto a carrier in the ultrasonic range. The ultrasonic couplers 69 can be, as shown in FIG. 11, ultrasonic transmitters and receivers which are locally separated from and connected via electrical lines to the electronic module 34, and which preferably are fixedly coupled to the skull bone in the mastoid area. The ultrasonic couplers, however, can also be integrated (not shown) in the electronic modules 34 when the electronic modules are implanted in the mastoid area such that ultrasonic conduction can take place through the skull bone.

Figure 12:
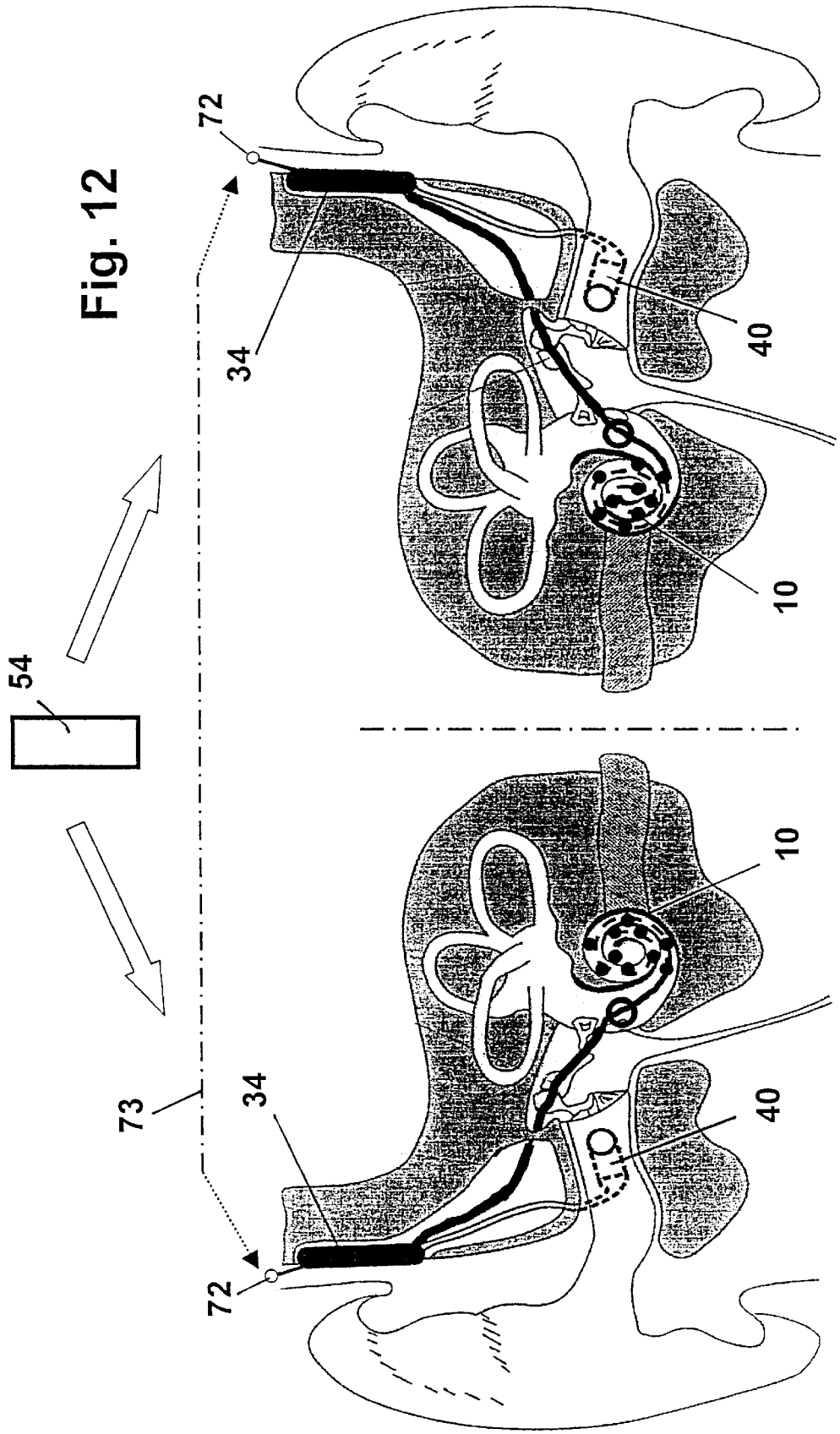
FIG. 12 shows a binaural application of a hearing implant as shown in FIG. 6 in which the signal processing modules communicate with one another via a transmission path which includes the tissue of the implant wearer.

A further modified embodiment of a binaurally designed hearing implant is shown in FIG. 12. In this embodiment, different from the embodiments of FIGS. 9 to 11, the bidirectional information, for example, digital, is preferably amplitude modulated or frequency modulated on the implant side onto a carrier and applied to the implanted electrodes 72 which are part of a data transmission path 73 which leads through the body tissue of the implant wearer. Thus, a modulated tissue current is obtained which, in a manner known per se (U.S. Pat. No. 5,113,859), provides for the desired communication between the signal processing modules 34 of the two system units.

A partially implantable system can also be binaurally applied and then provisions can be made for communication between the two system units, preferably according to the embodiments of binaural applications of totally implantable systems which are illustrated in FIGS. 9 to 12.

FIG. 13 shows another embodiment of a presently suitable intracochlear electromechanical transducer. The transducer structure shown in FIG. 13 corresponds to that of FIG. 2 except for the fact that the transducer 14' embedded in the carrier 11 is designed as a hollow cylinder. Application of a transducer AC voltage signal causes a dynamic volume change of the transducer which is indicated by broken lines. Here, use is made of the fact that a reduction in the volume of the hollow cylindrical transducer 14' reduces the inner volume of the transducer and, as a result, the intracochlear fluid 76 located there is pressed out of the cylinder cavity 77, as is indicated by the arrows 79. In the carrier 11, adjacent to the axial transducer ends, there are outlet openings 82 from which intracochlear fluid (arrows 79) is ejected when the transducer 14', as a result of an applied voltage signal, undergoes a reduction in volume and accordingly the above described pumping action is exerted on the intracochlear fluid. By corresponding dimensioning of the ratio between the enlarging and diminishing transducer surface and the opening surface of the outlet openings 82, a speed transformation can be achieved which, even for small volume changes of the transducer 14', allows formation of relatively high pressure changes in the area of the outlet openings 82.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

We claim:

1. An at least partially implantable system for rehabilitation of a hearing disorder which comprises:
    at least one acoustic sensor for picking up an acoustic signal and converting the acoustic signal into corresponding electrical signals,
    an electronic signal processing unit for audio signal processing and amplification,
    an electrical power supply unit which supplies individual components of the system with energy, and
    an output-side electromechanical transducer arrangement which is comprised of at least two independent and spatially separate transducers, an output-side of which is adapted for stimulation of fluid-filled inner ear spaces of a damaged inner ear of a patient in an implanted state,
    wherein the signal processing unit comprises driving signal processing electronics which electrically controls each of the transducers in a manner causing a traveling wave configuration to be formed on a basilar membrane of the damaged inner ear which approximates the manner of a traveling wave configuration of a healthy, undamaged inner ear.

2. The system of claim 1, wherein the transducers of the output-side electromechanical transducer arrangement are adapted to produce direct stimulation of the fluid-filled inner ear spaces of the damaged inner ear.

3. The system of claim 2, wherein the transducers of the output-side electromechanical transducer arrangement are output-side electromechanical transducers that are part of an intracochlear transducer array.

4. The system of claim 3, wherein the intracochlear transducer array has an outer diameter in a range from 0.4 mm to 2.0 mm.

5. The system of claim 3, wherein a total length of the intracochlear transducer array is between 5 mm and 50 mm.

6. The system of claim 3, wherein the intracochlear transducer array has a carrier of biocompatible material which is bio-stable in the inner ear.

7. The system of claim 6, wherein the electromechanical transducers are completely embedded in the carrier surrounded by a thin layer of the carrier material.

8. The system of claim 6, wherein mechanical attenuation elements are embedded in the carrier between the electromechanical transducers for minimizing mechanical wave propagation within the carrier between adjacent transducers.

9. The system of claim 8, wherein the attenuation elements are made of a material having a large mechanical impedance difference as compared to material of the carrier in order to achieve high attenuation values.

10. The system of claim 2, wherein the transducers of the extracochlear transducer array each have an output-side coupling element which is adapted to project through an opening of a cochlear wall into the fluid-filled inner ear space in an implanted state.

11. The system of claim 3, wherein the output-side electromechanical transducers in the transducer array are arranged in an equidistant distribution.

12. The system of claim 3, wherein the output-side electromechanical transducers in the transducer array are arranged at logarithmic distances according to a tonotopic frequency-location assignment.

13. The system of claim 12, wherein the transducer array comprises between 20 and 24 output-side electromechanical transducers in conformity with psychoacoustic critical bands.

14. The system of claim 1, wherein the transducers of the output-side electromechanical transducer arrangement are formed into an extracochlear array of output-side electromechanical transducers.

15. The system of claim 14, wherein the extracochlear transducer array is formed of Microsystems components.

16. The system of claim 15, wherein the extracochlear transducer array further comprises a substrate which contains a printed circuit electrical terminal panel for connection of a multipole, biocompatible implant lead to a module which contains driving signal processing electronics.

17. The system of claim 15, wherein the extracochlear transducer array further comprises a substrate which contains a printed circuit electronic module.

18. The system of claim 17, wherein the electronic module contains driver stages for controlling the output-side electromechanical transducers.

19. The system of claim 17, wherein the electronic module contains decoding logic and transducer modules for connection of a minimum pole implant lead.

20. The system of claim 19, wherein the array has a terminal comprised of a ground line, a data line and a clock signal line, and wherein supply of electrical operating energy takes place by phantom feed on the clock signal line.

21. The system of claim 19, wherein the array has a terminal comprised of a ground line, a data line and a clock signal line, and wherein supply of electrical operating energy takes place by rectifying the clock signal directly.

22. The system of claim 17, wherein the electronic module contains an interface module for digital data transmission via the implant lead.

23. The system of claim 17, wherein the electronic module contains corresponding digital-analog converters and driver modules assigned to the transducers for serial data transmission on the implant feed line.

24. The system of claim 17, wherein the extracochlear transducer array including the carrier structure is equipped with biocompatible coating.

25. The system of claim 17, wherein the output-side electromechanical transducers are piezoelectric transducers made of a material selected from the group consisting of lead zirconate titanate ceramics or polyvinylidene fluoride.

26. The system of claim 1, wherein the output-side electromechanical transducers are transducers selected from the group consisting of electromagnetic, electrodynamic, piezoelectric, magnetostrictive or dielectric transducers.

27. The system of claim 1, wherein the output-side electromechanical transducers are adapted to provide maximum deflection with minimum electric power consumption at a given transducer voltage.

28. The system of claim 1, wherein the transducers of the output-side electromechanical transducer arrangement have a transmission range from about 100 Hz to about 10 kHz.

29. The system of claim 1, wherein the transducers of the output-side electromechanical transducer arrangement are tuned to have first mechanical resonant frequency at an upper end of a desired transmission frequency range.

30. The system of claim 1, wherein the transducers of the output-side electromechanical transducer arrangement are hermetically sealed.

31. The system of claim 1, wherein the signal processing unit has a preprocessing arrangement designed for analog-digital conversion of the acoustic sensor signals and for at least one function selected from the group consisting of pre-amplification or filtering of the acoustic sensor signals.

32. The system of claim 31, wherein the preprocessing arrangement comprises an antialiasing filter.

33. The system of claim 1, wherein said at least one acoustic sensor comprises a plurality of acoustic sensors, each of which has analog-digital converter associated therwith.

34. The system of claim 1, wherein the signal processing unit comprises software modules adapted to mask tinnitus during operation of the system.

35. The system of claim 34, wherein a preprogrammed read-only memory area is assigned to the signal processor.

36. The system of claim 1, comprising at least one digital-analog converter connected to an input of the output-side electromechanical transducer arrangement.

37. The system of claim 1, wherein the signal processing electronics comprise software modules which control the output-side electromechanical transducer arrangement achieving spectral, time, amplitude- and phase-referenced transducer signal properties that are dimensioned so as to produce, in an implanted state, a traveling wave at a basilar membrane of the damaged inner ear that approximates that of healthy hearing.

38. The system of claim 37, wherein the software modules are static software modules which are stored in a program storage of the digital signal processor and remain unchanged.

39. The system of claim 37, comprising a wireless telemetry means for transmission of data between the implanted part of the system and an external unit, wherein the software modules are adaptive, being changeable after being stored in a program storage of the digital signal processor.

40. The system of claim 39, wherein the software modules are adaptive for parameter matching in an implanted stated by training conducted by an implant wearer.

41. The system of claim 1, wherein the signal processing unit comprises a digital signal processor which provides for at least one function selected from the group consisting of processing analog-digital-converted acoustic sensor signals or generation of digital signals for tinnitus masking.

42. The system of claim 41, comprising a microprocessor module for control of at least one of a digital-analog converter, said analog-digital converter, and said signal processor, via a data bus.

43. The system of claim 42, wherein an implantable storage arrangement for storage of an operating program for the microprocessor module is assigned to the microprocessor module, and at least one of a plurality of parts of the operating program for the microprocessor module are adapted to be replaced by data transferred from the external unit via the telemetry means.

44. The system of claim 1, wherein the signal processing unit comprises a software module for approximate simulation of a healthy cochlear amplifier based on an adaptive neural network.

45. The system of claim 44, wherein the principle of time-reversed acoustics is implemented in the neural network for simulation of a healthy cochlear amplifier, and control of the output-side electromechanical transducers takes place by time-reversed acoustics such that locally limited areas of the cochlea are mechanically stimulated.

46. The system of claim 1, comprising a wireless telemetry means for transmission of data between the implanted part of the system and an external unit.

47. The system of claim 46, comprising a microprocessor module for control of at least one of a digital-analog converter, an analog-digital converter, and said signal processing unit via a data bus, wherein at least one of a plurality of program parts are adapted to be transferred between an external source, the microprocessor module and the signal processor via the data bus and the telemetry means.

48. The system of claim 46, wherein the telemetry means is adapted transmission of operating parameters between the implantable part of the system and the external unit.

49. The system of claim 46, wherein a rewritable implantable storage arrangement is assigned to the signal processor for storage and retrieval of an operating program and at least parts of the operating program are adapted to be at least partially replaced by data transmitted from the external unit via the telemetry means.

50. The system of claim 49, comprising at least two storage areas for storage and retrieval of at least said operating program of the signal processor.

51. The system of claim 49, further comprising a buffer storage arrangement in which data transmitted from the external unit via the telemetry means are buffered before being relayed to the signal processor.

52. The system of claim 51, further comprising a checking logic for checking data stored in the buffer storage arrangement before said data are relayed to the signal processor.

53. The system of claim 52, comprising a microprocessor module for control of at least one of a digital-analog converter, said analog-digital converter, and said signal processing unit, via a data bus; wherein the checking logic and the buffer storage arrangement are implemented in the microprocessor module.

54. The system of claim 51, wherein the buffer storage arrangement comprises at least two storage areas for storage and retrieval of data transferred from the external unit via the telemetry means.

55. The system of claim 1, wherein the electrical power supply unit comprises an implantable rechargeable energy storage element, and wherein the system is totally implantable except for a wireless, transcutaneous charging device which is provided for charging of the storage element.

56. The system of claim 55, comprising a wireless remote control for control of implant functions by the implant wearer.

57. The system of claim 1, wherein the system is partially implantable, wherein said at least one acoustic sensor, said electronic arrangement for audio signal processing and amplification, said power supply unit and a modulator/transmitter unit is contained in an external module to be worn externally on the body a user, and wherein the electromechanical transducer arrangement is an implantable passive unit which receives operating energy and transducer control data via the modulator/transmitter unit in the external module.

58. The system of claim 1, wherein the system is a binaural system for rehabilitation of a hearing disorder of both ears and has two system units, one each for each of two ears of a wearer.

59. The system of claim 58, wherein the two system units are essentially equal to one another.

60. The system of claim 58, wherein one system unit is master unit and the other system unit is slave unit which is controlled by the master unit.

61. The system of claim 58, comprising a wired implantable line connection by which the signal processing modules communicate with one another for optimizing binaural signal processing and transducer array control in both system units.

62. The system of claim 58, comprising a wireless connection by which the signal processing modules communicate with one another for optimizing binaural signal processing and transducer array control in both system units.

63. The system of claim 58, wherein the signal processing unit of both system units communicate with one another via an ultrasonic path adapted to be coupled, in an implanted stated, by bone conduction for optimizing binaural signal processing and transducer array control in both system units.

64. The system of claim 58, wherein implantable electrodes are assigned to the signal processing unit and the implantable electrodes are adapted, in the implanted state, to form part of a data transmission path body tissue of the implant wearer for communication of the signal processing units of the two system units.

65. The system of claim 1, wherein said at least one electromechanical transducer is hollow body adapted to undergo a dynamic volume change when a voltage signal is applied.

66. The system of claim 1, wherein said at least one electromechanical transducer is housed in a hose-shaped carrier which is provided with at least one opening for the passage of intracochlear fluid, said at least one opening being adjacent to at least one end of the transducer.

* * * * *